US009958409B2

(12) United States Patent
Gerber et al.

(10) Patent No.: US 9,958,409 B2
(45) Date of Patent: May 1, 2018

(54) SYSTEMS AND METHODS FOR MULTIPLE ANALYTE ANALYSIS

(71) Applicant: Roche Diabetes Care, Inc., Indianapolis, IN (US)

(72) Inventors: Martin T. Gerber, Carmel, IN (US); Eric Diebold, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 524 days.

(21) Appl. No.: 14/549,659

(22) Filed: Nov. 21, 2014

(65) Prior Publication Data

US 2015/0076004 A1     Mar. 19, 2015

Related U.S. Application Data

(62) Division of application No. 13/667,154, filed on Nov. 2, 2012, now Pat. No. 8,920,628.

(51) Int. Cl.
*G01N 27/327* (2006.01)
*G01N 27/30* (2006.01)
(Continued)

(52) U.S. Cl.
CPC ......... *G01N 27/307* (2013.01); *A61B 5/0002* (2013.01); *A61B 5/1486* (2013.01);
(Continued)

(58) Field of Classification Search
CPC ...... G01N 33/492; G01N 33/66; G01N 27/48; G01N 27/26; G01N 27/327–27/3274; C12Q 1/54; A61B 1/14532; A61B 1/0002
See application file for complete search history.

(56) References Cited

U.S. PATENT DOCUMENTS

| 4,397,956 A | 8/1983 | Maggio |
| 5,071,769 A | 12/1991 | Kundu et al. |

(Continued)

FOREIGN PATENT DOCUMENTS

| CN | 201438187 U | 4/2010 |
| EP | 279069 | 7/1994 |

(Continued)

OTHER PUBLICATIONS

T. M.Wallace, et al. "The hospital and home use of a 30-second hand-held blood ketone meter: guidelines for clinical practice" Diabetic Medicine, vol. 18, No. 8, Aug. 2001, p. 640-645.*

(Continued)

*Primary Examiner* — J. Christopher Ball

(57) ABSTRACT

Systems and methods for multiple analyte analysis are provided. In one embodiment, a method includes determining concentrations of first and second analytes in a sample. The first and second analytes may be, for example, glucose and hydroxybutyrate. In this form, an indication related to the measured concentration of hydroxybutyrate is provided in response to determining that the concentration of hydroxybutyrate is above a predetermined value. In a further aspect of this form, a quantitative indication representative of the measured glucose concentration is automatically provided regardless of the value of the measured glucose concentration. In another embodiment, a system includes a meter configured to interact with a test element to assess first and second analytes in a sample. Further embodiments, forms, objects, features, advantages, aspects, and benefits shall become apparent from the description and drawings.

7 Claims, 12 Drawing Sheets

(51) Int. Cl.

| | | |
|---|---|---|
| *C12Q 1/54* | (2006.01) | |
| *A61B 5/00* | (2006.01) | |
| *G01N 33/49* | (2006.01) | |
| *G01N 33/66* | (2006.01) | |
| *A61B 5/145* | (2006.01) | |
| *A61B 5/1486* | (2006.01) | |

(52) U.S. Cl.
CPC ............ *A61B 5/14532* (2013.01); *C12Q 1/54* (2013.01); *G01N 27/327* (2013.01); *G01N 27/3272* (2013.01); *G01N 27/3273* (2013.01); *G01N 33/492* (2013.01); *G01N 33/66* (2013.01); *A61B 2562/0295* (2013.01)

(56) References Cited

U.S. PATENT DOCUMENTS

| | | | |
|---|---|---|---|
| 5,633,143 | A | 5/1997 | Ueda et al. |
| 5,997,817 | A | 12/1999 | Crismore et al. |
| 6,540,891 | B1 | 4/2003 | Stewart et al. |
| 6,541,216 | B1 | 4/2003 | Wilsey et al. |
| 6,736,957 | B1 | 5/2004 | Forrow et al. |
| 6,762,035 | B1 | 7/2004 | Gupta |
| 6,984,307 | B2 | 1/2006 | Zweig |
| 7,504,019 | B2 | 3/2009 | Forrow et al. |
| 7,553,615 | B2 | 6/2009 | Heindl et al. |
| 7,727,467 | B2 | 6/2010 | Burke et al. |
| 8,008,037 | B2 | 8/2011 | Wilsey et al. |
| 2004/0118704 | A1 | 6/2004 | Wang et al. |
| 2005/0136471 | A1 | 6/2005 | Bhullar et al. |
| 2007/0289881 | A1 | 12/2007 | Forrow et al. |
| 2008/0213809 | A1 | 9/2008 | Heindl et al. |
| 2010/0075359 | A1 | 3/2010 | Toranto et al. |
| 2010/0255497 | A1 | 10/2010 | Toranto et al. |
| 2010/0268043 | A1 | 10/2010 | Yodfat et al. |
| 2010/0270175 | A1 | 10/2010 | Pei et al. |
| 2011/0031133 | A1 | 2/2011 | Forrow et al. |
| 2011/0079522 | A1 | 4/2011 | Webster et al. |
| 2011/0094882 | A1 | 4/2011 | Macfie et al. |
| 2011/0094896 | A1 | 4/2011 | Macfie et al. |
| 2011/0143416 | A1 | 6/2011 | Horn et al. |
| 2011/0288884 | A1 | 11/2011 | Algoo et al. |
| 2012/0165683 | A1 | 6/2012 | Kono et al. |

FOREIGN PATENT DOCUMENTS

| | | |
|---|---|---|
| EP | 1023455 | 5/2007 |
| EP | 1801229 | 6/2007 |
| EP | 2308991 | 4/2011 |
| EP | 2317313 | 4/2011 |
| EP | 2317315 A1 | 5/2011 |
| EP | 2335568 A2 | 6/2011 |
| JP | 20003533318 A | 11/2003 |
| WO | 2001/073114 | 10/2001 |
| WO | 2001/081890 A3 | 11/2001 |
| WO | 2011/123305 | 10/2011 |
| WO | 2012/003306 | 1/2012 |

OTHER PUBLICATIONS

MediSense Precision Xtra(TM) Advanced Diabetes Management System, User's Guide, Abbott Laboratories, Abbott Diabetes Care, Aug. 2005, p. 1-90 (Year: 2005).*
http://novabiomedical.com/products/strip_based_clinical_analyzers/statstrip.php; StatStrip Glucose StatStrip Xpress Glucose; Nova Biomedical—Statstrip.
FreeStyle User Manual (Mar. 2011 Revision).

* cited by examiner

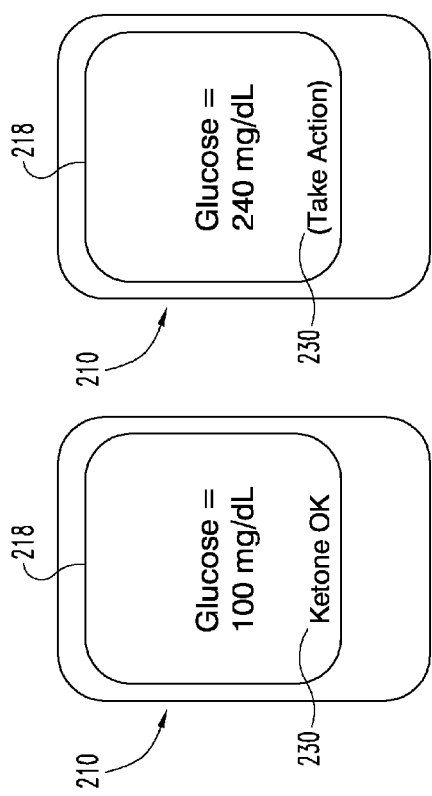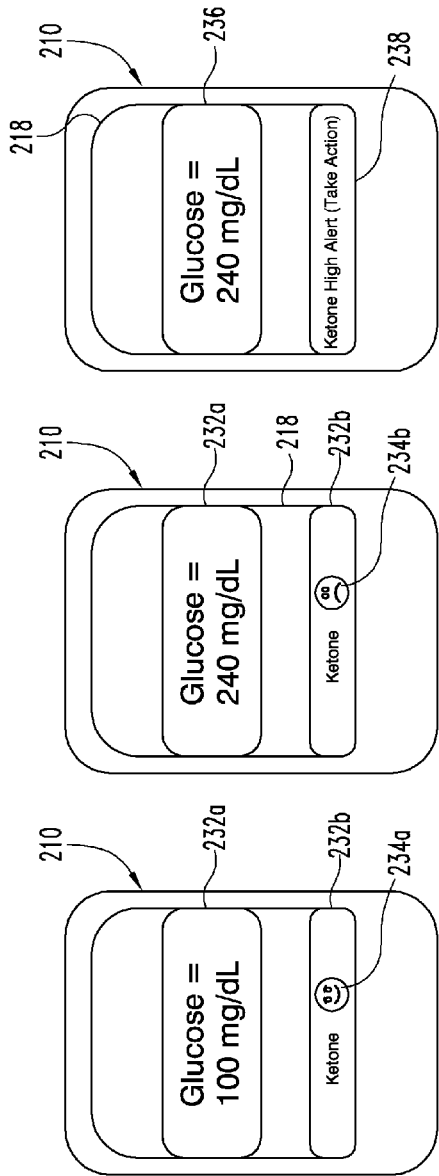

SYSTEMS AND METHODS FOR MULTIPLE ANALYTE ANALYSIS

CROSS-REFERENCE TO RELATED APPLICATIONS

This patent application is a divisional of U.S. patent application Ser. No. 13/667,154 (filed 2 Nov. 2012), which is incorporated herein by reference as if set forth in its entirety.

BACKGROUND

The use of disposable test elements has become commonplace to measure the presence and/or concentrations of selected analytes in test samples. For example, patients suffering from diabetes and similar medical conditions often engage in self-monitoring of blood glucose where the patient monitors his or her blood glucose levels. The purpose of monitoring blood-glucose levels is to determine the concentration level, and if necessary to take corrective action if the level is too high or too low in order to bring the level back within an acceptable range. In addition, blood glucose levels are determined to calculate a pre-meal insulin bolus often with the help of a bolus calculator with the goal of minimizing glucose increases from consumption of the meal. The failure to take corrective action can have serious medical implications. Glucose monitoring is a fact of everyday life for diabetic individuals, and the accuracy of such monitoring can literally mean the difference between life and death. Failure to maintain blood glucose at acceptable levels on a regular basis can result in serious diabetes-related complications, including cardiovascular disease, kidney disease, nerve damage and blindness.

People with diabetes who intensively manage their blood sugar experience long-lasting benefits. The Diabetes Control and Complications Trial (DCCT) was a clinical study conducted from 1983 to 1993 by the National Institute of Diabetes and Digestive and Kidney Diseases (NIDDK). The DCCT compared intensive to conventional treatments. Patients on intensive treatment kept glucose levels as close to normal as possible with at least three insulin injections a day or an insulin pump, and frequent self-monitoring of blood glucose levels. Intensive treatment aimed to keep hemoglobin A1c (HbA1c), which reflects average blood glucose over a 2- to 3-month period, as close to normal as possible. Conventional treatment consisted of one or two insulin injections a day with once-a-day urine or blood glucose testing. The results of the DCCT study showed that keeping blood glucose levels as close to normal as possible slows the onset and progression of eye, kidney, and nerve diseases caused by diabetes. In fact, it demonstrated that any sustained lowering of blood glucose helps, even if the person has a history of poor control.

A number of analytical instruments or biosensors, such as glucose meters, are currently available that permit an individual to test the glucose level in a small sample of blood. Many of the meter designs currently available make use of a disposable test element which, in combination with the meter, measures the amount of glucose in the blood sample electrochemically or optically. In current glucose meters, the information displayed as a consequence of a successful blood glucose measurement is the respective blood glucose value, typically shown in mg/dL or mmol units, and perhaps the time and date the measurement was performed. This information, in combination with calculation of planned or known intake of carbohydrates or planned or known activities and knowledge of other situational or individual factors, is in most cases sufficient to allow diabetics to adjust or derive their dietary intake and/or an immediate dose of insulin to inject to control blood glucose level on the short-term. Also, in case of low glucose values, diabetics can detect the need for intake of sugar to avoid hypoglycemia.

An absence or insufficient amount of insulin prevents the body from using glucose as a fuel source to produce energy. When this occurs, the body produces energy by breaking down fatty acids, which results in ketone byproducts and increased ketone levels. Increased ketone levels in diabetics may also be caused by a heart attack, stroke, recreational drug usage or an intercurrent illness such as pneumonia, influenza, gastroenteritis, or a urological infection. Excessive ketone levels in diabetics leads to an episode of diabetic ketoacidosis (DKA), a medical emergency that can result in death if not treated. Symptoms of DKA include nausea, vomiting, excessive thirst and urine production, abdominal pain, labored breathing, fatigue, and coma, amongst others. Given the seriousness of DKA, it is desirable to administer treatment to reduce ketone levels before the full onset of a DKA episode. Further, since symptoms related to a DKA episode may not present until the DKA episode has onset or ketone levels are otherwise undesirably high, it is generally preferred for ketone reducing treatment not to begin as a response to these symptoms.

Prevention of DKA episodes can be achieved by measuring ketone levels and seeking medical attention if they rise above a certain concentration. The ADA website recommends that ketone levels should be checked every 4-6 hours when a diabetic has an illness (such as a cold or the flu), or when his or her blood glucose is more than 240 mg/dl. (See http://www.diabetes.org/living-with-diabetes/complications/ketoacidosis-dka.html). Urine tests can be utilized to determine ketone levels. However, for diabetics who perform multiple blood glucose tests per day, performing separate urine tests in addition to their blood glucose tests is time consuming and burdensome.

By having a dual test to measure glucose and ketone levels on the same test strip, a diabetic is better enabled to comply with testing recommendations and safer therapy by detecting high ketone levels early. For example, it is recommended to avoid exercise when ketone and blood glucose are high because elevated levels of these analytes may be indicative of unsatisfactory diabetes management. However, most diabetics do not have ketone tests readily available for testing, and often do not have information readily available for how to handle such situations. Furthermore, the symptoms of diabetic ketoacidosis usually evolve over about a 24 hour period, meaning useful information and instruction typically require the perspective of trending analysis.

The use of separate urine tests for determining ketone levels also requires additional diagnostic supplies and their attendant costs, and makes it difficult to correlate blood glucose and ketone levels. It is also possible to determine ketone levels from blood samples. When blood samples are used, ketone levels are commonly determined by measuring the concentration of hydroxybutyrate, which is the predominate ketone in blood. Hydroxybutyrate concentrations below 0.6 mM in blood are considered normal, while hydroxybutyrate concentrations that are between 0.6 mM and 1.5 mM indicate that a problem may develop and greater than 1.5 mM indicate a risk for developing DKA. Hydroxybutyrate concentrations above 3 mM in blood are indicative of DKA and require emergency medical treatment.

Current techniques for determining ketone levels from blood involve single function test elements that are suitable for detecting hydroxybutyrate concentrations for example. Much like the urine test described above however, diabetics who perform a relatively high magnitude of blood glucose tests per day may find it time consuming and burdensome to perform separate ketone level blood tests in addition to their blood glucose tests, particularly since current blood ketone tests are slower than state of the art blood glucose tests. Ketone level blood tests that are performed independent of blood glucose tests also require additional diagnostic supplies and additional expenses attendant therewith must be incurred. Moreover, performing separate tests for determining blood glucose and blood ketone levels makes it difficult to correlate the measured blood glucose and blood ketone values since, amongst other factors, they may not be measured within the same timeframe or may be performed using different devices.

Other techniques for determining ketone levels from blood involve test elements suitable for detecting blood glucose and blood ketone levels. In these current test elements however, blood glucose levels are measured more quickly than blood ketone levels such that the blood ketone test results are delayed and provided after the blood glucose test results. Alternatively, the results of both the blood glucose and blood ketone tests are not provided until the latter completion of the blood ketone test. In either case, waiting for the results of one or both tests until the blood ketone test is completed can become quite burdensome and time consuming for a diabetic who performs a relatively high magnitude of tests each day, particularly when considering that in some instances the blood ketone test can take almost twice as long to complete as the blood glucose test. Moreover, when the blood glucose test results are provided before and separate from the blood ketone test results, a possibility arises for a user to discontinue testing before the blood ketone test is completed and/or divert attention elsewhere after the blood glucose test results have been provided but before the results of the blood ketone test have been properly considered. In further instances, a user may be burdened by the automatic display of the blood ketone results following each test, which may lead to insufficient consideration or user depreciation of the importance of the blood ketone test results. As a corollary, burdening a diabetic patient with a ketone value for each measurement even when the majority of time it is in a normal range could cause a user to ignore the value at a time when it really requires attention.

Given the ramifications of accurate recording, reporting and analyzing of blood ketone measurements in addition to blood glucose measurements, improvements in the techniques, procedures and equipment for testing blood ketone levels and/or blood ketone and blood glucose levels are desired.

SUMMARY

Systems and methods for multiple analyte analysis are provided. In one embodiment, a method includes determining concentrations of first and second analytes in a sample. The first and second analytes may be, for example, glucose and a ketone such as hydroxybutyrate. For reference in this application, the term "ketone" is understood to refer to and include ketone bodies such as hydroxybutyrate. In this form, an indication related to the measured concentration of hydroxybutyrate is provided in response to determining that the concentration of hydroxybutyrate is above a predetermined value. In a further aspect of this form, a quantitative indication representative of the measured glucose concentration is automatically provided regardless of the value of the measured glucose concentration. In a yet further aspect, each measured concentration of hydroxybutyrate is stored or otherwise retained regardless of whether that measured concentration is above a predetermined value in order to permit trending analysis to be conducted with respect to all measured concentrations of hydroxybutyrate. In another embodiment, a system includes a meter configured to interact with a test element to assess first and second analytes in a sample. Other aspects of the subject application are directed to unique techniques for analyzing analytes in a sample. Further embodiments, forms, objects, features, advantages, aspects, and benefits shall become apparent from the description and drawings.

In an additional embodiment, a method includes providing a test element configured for analyzing first and second analytes in a sample; contacting the test element with the sample; determining concentration of the first analyte in the sample and providing an indication in response to determining the first analyte concentration is above a predetermined value; and determining concentration of the second analyte in the sample. In one form, the method further includes displaying information corresponding to the second analyte concentration. In another form, the first analyte is hydroxybutyrate and the second analyte is glucose. In still another form, the predetermined value is 0.6 mM. In another form, the step of providing the indication in response to determining the first analyte concentration is above a predetermined value includes at least one of displaying the first analyte concentration, providing a warning, providing a list of actions to take in response to the first analyte concentration being above the predetermined value, and transmitting a message to at least one of a user of the test element, healthcare provider, caregiver and parent or guardian.

In yet another form of this embodiment, providing the indication in response to determining the first analyte concentration is above the predetermined level includes transmitting a message to a mobile device or computer. In one aspect of this form, providing the indication in response to determining the first analyte concentration is above the predetermined level further includes displaying a message related to the first analyte concentration on a test meter. In another form, providing the indication in response to determining the first analyte concentration is above the predetermined level includes displaying a message related to the first analyte concentration. In one other form, providing the indication in response to determining the first analyte concentration is above the predetermined level includes changing a color or a shading of at least a portion of a display screen or textual display. In still another form, providing the indication in response to determining the first analyte concentration is above the predetermined level includes displaying an information icon on a display screen. In still another form, providing the indication in response to determining the first analyte concentration is above the predetermined level includes displaying an information icon on a display screen with an audio tone or vibration to encourage the patient to take notice. In one aspect of this form, the method further includes providing a message in response to a selection of the information icon. In a further aspect, the message includes at least one of a description of the first analyte concentration, a list of actions to take in response to the first analyte concentration being above the predetermined level, and contact information of a healthcare provider.

In another embodiment, a system includes a test element configured for analyzing first and second analytes in a sample. The system also includes a meter configured to interact with the test element and including a controller structured to: determine concentration of the first analyte in the sample and, if the concentration of the first analyte is above a predetermined value, provide a first signal for providing an indication related thereto; and determine concentration of the second analyte in the sample and provide a second signal for outputting information related to the concentration of the second analyte. In one form of this embodiment, the indication includes at least one of outputting information corresponding to the concentration of the first analyte, providing a warning, providing a list of actions to take in response to the first analyte concentration being above the predetermined value, and transmitting information related to the concentration of the first analyte to at least one of a user of the system, healthcare provider, caregiver and parent or guardian. In another form, the first analyte is hydroxybutyrate and the second analyte is glucose. In one aspect of this form, the predetermined value is in the range of 0.5 mM to 3.0 mM.

In another form of this embodiment, the meter further includes a display responsive to the first signal to display the indication related to the concentration of the first analyte. In one aspect of this form, the display is responsive to the first signal to provide an icon related to the concentration of the first analyte. In another aspect of this form, at least a portion of the display is configured to change color or shading in response to the first signal. In yet another aspect of this form, the display is configured to provide an information icon in response to the first signal. In a further aspect, the display is further configured to provide a message in response to a selection of the information icon, the message including at least one of a description of the first analyte concentration, a list of actions to take in response to the first analyte concentration being above the predetermined level, and contact information of a healthcare provider. In still another form of this embodiment, the meter further includes a communication module configured to transmit a message to a mobile device or computer in response to the first signal. In yet another form, the controller is further structured to provide a third signal for providing an approval indication if the concentration of the first analyte is below the predetermined value.

In a further embodiment, a method includes performing a plurality of tests to determine concentrations of first and second analytes in a sample. Each of the tests includes applying the sample to a test element configured for analyzing the first and second analytes in the sample. The method also includes storing the first analyte concentration determined from each test performed; analyzing the stored concentrations of the first analyte to monitor for an existence of any trends in the stored concentrations, such as toward a predetermined value or upwardly increasing over time, or as between common time periods such as specific time of day, weekend trends, or after specific events like meals, exercise or illness, and any interesting rate-of-change trends suggesting concerning changes in ketone/hydroxybutyrate levels regardless of whether any such levels are measured to be above a predetermined value; and providing a first indication in response to detecting the existence of the trend. The rate-of-change value to trigger a trend can be a preselected value or one that can be set by a person with diabetes or health care providers within reasonable ranges. In one form, the method also includes providing a second indication in response to determining the first analyte concentration is above the predetermined value in any one or more of the plurality of tests. In one aspect of this form, the method further includes automatically providing a third indication related to the concentration of the second analyte after performing each of the tests. In a further aspect, the first analyte is hydroxybutyrate and the second analyte is glucose.

In another form of this embodiment, the first indication includes one of a graphical illustration of the trend and an information icon. In still another form, providing the first indication includes displaying an information icon on a meter display. In another form, the method further includes providing a graphical illustration of the trend in response to a selection of the information icon. In another form of this embodiment, a graphical illustration of a trend is shown automatically if the trend meets some pre-specified criteria. Such criteria could be for example: one or more measured values coming close to or exceeding a pre-specified hydroxybutyrate value, the max/min hydroxybutyrate level over the past days/weeks/months is greater than a pre-specified value, or other criteria such as initiation of a "ketone watch" or measured values trending toward initiation of a "ketone watch".

A ketone watch may be set by the meter whenever a measured glucose value greater than or equal to a predetermined value, such as 240 mg/dL, is recorded. The ketone watch would recommend testing glucose and hydroxybutyrate every 4-6 hours as long as the glucose value exceeds the predetermined value. In one non-limiting form for example, upon initiation of and during the ketone watch, the meter may automatically display measured glucose and hydroxybutyrate levels regardless of their relationship with any pre-specified values. A ketone watch may also start a new trending set of data to determine if hydroxybutyrate levels are beginning to rise even if still below the threshold of a high hydroxybutyrate level. A ketone watch may also be started if the user has indicated they have an illness such as a cold or the flu.

In still another embodiment, a method includes providing a hand held device including a display, a processor and a storage memory. The device is operative to engage one or more test elements and to determine concentration of at least first and second analytes in a fluid sample provided on the one or more test elements. The method also includes: using the device, recording in the storage memory the value of the determined concentration of each of the at least first and second analytes; using the device, determining whether the determined concentration for the first analyte is above a first predetermined value; using the device, determining whether the determined concentration for the second analyte is above a second predetermined value; and using the device, activating a watch mode when the determined concentration for either of the first and second analytes is above the respective first and second predetermined values.

In one form of this embodiment, the storage memory includes a plurality of recorded values of determined concentrations for each of the first and second analytes, and the method further includes: selecting at least one of the first and second analytes for monitoring trending information; using the device, determining whether the trending information for the analyte selected for monitoring generally matches predetermined criteria for recommending an increased frequency for determining the concentration for the analyte selected; and using the device, activating the watch mode regardless of the determined concentration for either of the first and second analytes being above the respective first and second predetermined values when the trending information generally matches the predetermined criteria. In one aspect of this form, the first analyte is hydroxybutyrate and the second analyte is glucose, and the analyte selected for monitoring comprises hydroxybutyrate.

In another form of this embodiment, the watch mode comprises the device providing at least one recommendation for an increased frequency for determining the concentration for at least one of the first and second analytes. In yet another form, the method further includes, when the watch mode is activated, displaying a visual indication on the display, the visual indication configured to indicate the activation of the watch mode. In another form of this method, the first analyte is hydroxybutyrate and the second analyte is glucose. In one non-limiting form, one or more of the embodiments described above may involve a test element that includes a first coenzyme-dependent enzyme or a substrate for the first enzyme and a second coenzyme-dependent enzyme or a substrate for the second enzyme. The test element also includes a coenzyme selected from the group consisting of thio-NAD, thio-NADP, and a compound according to formula (I):

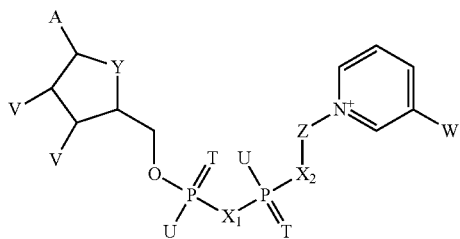
(I)

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof.

In one aspect, the first analyte is hydroxybutyrate and the first enzyme is a hydroxybutyrate dehydrogenase. In a further aspect, the hydroxybutyrate dehydrogenase is 3-hydroxybutyrate dehydrogenase. In a further aspect, the second enzyme is a dehydrogenase selected from the group consisting of glucose dehydrogenase, lactate dehydrogenase, malate dehydrogenase, glycerol dehydrogenase, alcohol dehydrogenase, sorbitol dehydrogenase, and an amino acid dehydrogenase comprising L-amino acid dehydrogenase. In still another aspect, the second analyte is glucose and the second enzyme is a glucose dehydrogenase or a glucose oxidase. In a further aspect, the coenzyme is a compound according to formula (I)

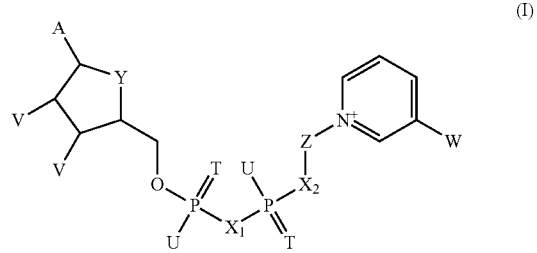
(I)

in which
A=adenine,
T=in each case denotes O,
U=in each case denotes OH,
V=in each case denotes OH,
W=$CON(R)_2$ in which R denotes H,
$X_1$=O,
$X_2$=O,
Y=O, and
Z=a carbocyclic 5-membered ring of the general formula (II)

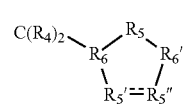
(II)

in which a single bond is present between R5' and R5", and in which
R4=H,
R5'=CHOH,
R5"=CHOH,
R5=$CR4_2$,
R6=CH, and
R6'=CH.
In yet another further aspect, the coenzyme is a compound according to formula (I)

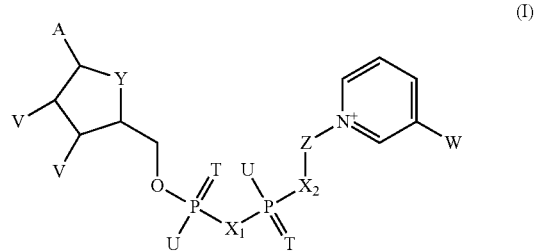
(I)

in which
A=adenine,
T=in each case denotes O,
U=in each case denotes OH,
V=in a first case denotes OH and in a second case denotes a phosphate group,
W=$CON(R)_2$ in which R denotes H,
$X_1$=O,
$X_2$=O,
Y=O, and
Z=a carbocyclic 5-membered ring of the general formula (II)

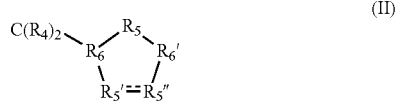

in which a single bond is present between R5' and R5", and in which
R4=H,
R5'=CHOH,
R5"=CHOH,
R5=CR4$_2$,
R6=CH, and
R6'=CH.

In still another further aspect, the coenzyme is thio-NAD. In another further aspect, the coenzyme is thio-NADP.

In a further aspect, the test element includes a first reagent material which includes the first enzyme or the substrate for the first enzyme, and the coenzyme selected from the group consisting of thio-NAD, thio-NADP and the compound according to formula (I) or a salt or optionally a reduced form thereof. In a further aspect, the test element also includes a second reagent material which includes the second enzyme or the substrate for the second enzyme, and a coenzyme selected from the group consisting of FAD, NAD, NADP and the compound according to formula (I) or a salt or optionally a reduced form thereof. In a further aspect, the test element includes a test strip configured to carry the first and second reagent materials. In yet another further aspect, the test strip includes a first electrode system associated with the first reagent material and a second electrode system associated with the second reagent material. In another aspect, the first reagent material further includes an electrochemical mediator or mediator precursor such as one of nitrosoaniline, potassium ferricyanide, a phenazine derivative, or hexaammineruthenium chloride or a combination thereof.

Further, although the description hereof discloses the use of a convenient dual test of ketone and glucose, persons of skill in the art will appreciate that other multi-analyte test strips may also be beneficial as a dual test with glucose and analytes such as 1,5 anhydroglucitol or HbA1c.

Another aspect of the present application is a unique technique for measuring the presence and/or concentration of multiple analytes in test samples. Other aspects include unique methods, systems, devices, kits, assemblies, equipment, and/or apparatus related to analyte detection in a sample.

Further aspects, embodiments, forms, features, benefits, objects, and advantages shall become apparent from the detailed description and figures provided herewith.

BRIEF DESCRIPTION OF THE FIGURES

FIGS. 6A-6B are schematic illustrations of one non-limiting display configuration for the analytical instrument.

FIGS. 7A-7B are schematic illustrations of another non-limiting display configuration for the analytical instrument.

FIG. 8 is a schematic illustration of yet another non-limiting display configuration for the analytical instrument.

DETAILED DESCRIPTION OF THE ILLUSTRATED EMBODIMENTS

Figure 1:
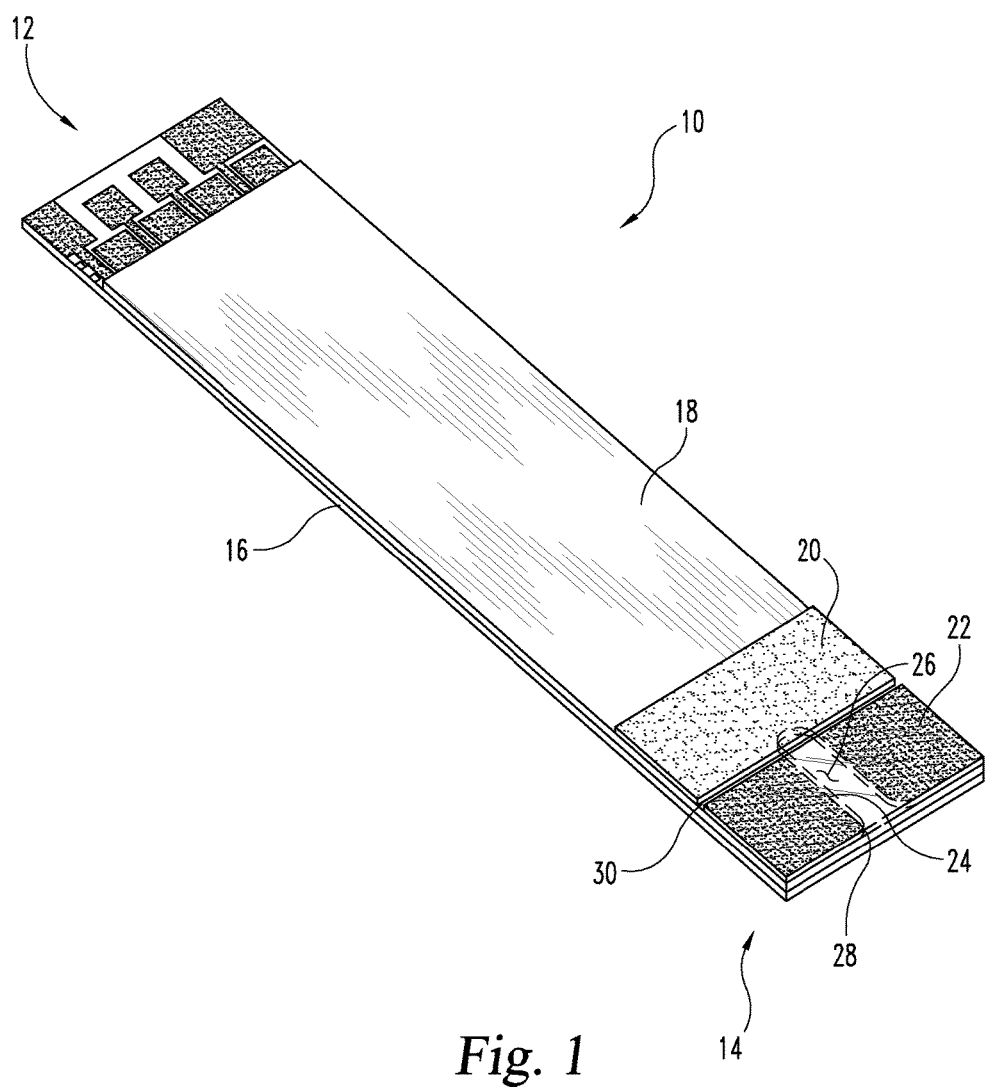
FIG. 1 is a perspective view of a first embodiment test element.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Systems and methods for multiple analyte analysis are provided. In one embodiment, a method includes determining concentrations of first and second analytes in a sample. The first and second analytes may be, for example, glucose and hydroxybutyrate. In this form, an indication related to the measured concentration of hydroxybutyrate is provided in response to determining that the concentration of hydroxybutyrate is above a predetermined value. In a further aspect of this form, a quantitative indication representative of the measured glucose concentration is automatically provided regardless of the value of the measured glucose concentration. In another embodiment, a system includes a meter configured to interact with a test element to assess first and second analytes in a sample. This assessment may range from detecting the presence of the first and second analytes to determining the concentration of the first and second analytes. Further aspects and features of the present application are described with respect to the illustrated embodiments as follows.

Figure 2:
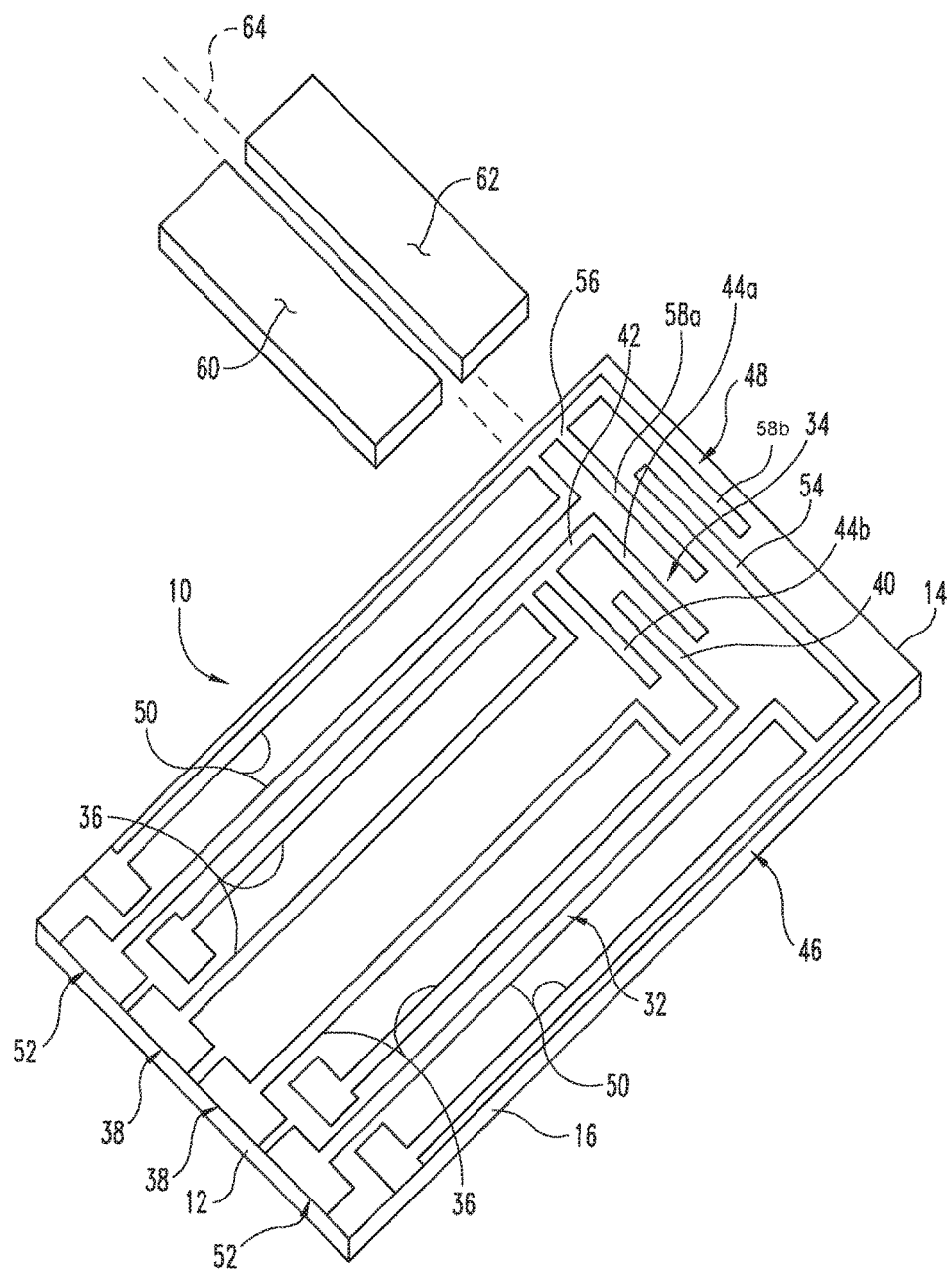
FIG. 2 is an exploded, perspective view of various features of the test element of FIG. 1.

Referring to FIGS. 1 and 2, further details of a first embodiment test element 10 configured for assessing first and second analytes in a sample will now be provided. Test element 10 is provided as an electrochemical sensor including a sample-receiving chamber for the sample fluid, and first and second reagent materials for producing electrochemical signals in the presence of the first and second analytes. In the illustrated form, test element 10 extends between a meter insertion end 12 and a dosing end 14. In one non-illustrated form, the shape of dosing end 14 may be distinguishable from meter insertion end 12 so as to aid users in proper handling and use of test element 10. Test element 10 may also include one or more graphics (not shown) to provide a user guidance on proper handling and use.

Test element 10 is provided in the form of a disposable test strip which has a laminar construction including a base substrate 16, a spacing layer 18, a body cover 20 and a chamber cover 22. Further details of test elements including a similar laminar construction are provided in U.S. Pat. No. 7,727,467, the contents of which are incorporated herein by reference in their entirety. Spacing layer 18 includes a void portion 24 to provide a sample-receiving chamber 26 extending between base substrate 16 and body cover 20 and chamber cover 22. In this configuration, sample-receiving chamber 26 opens at dosing end 14 of test element 10 through an opening 28 which is configured to facilitate passage of a sample fluid into sample-receiving chamber 26. Forms in which sample-receiving chamber 26 opens through an opening positioned along a side of test element 10 are also contemplated. Further, forms in which the sample-receiving chamber 26 opens through an opening positioned along the full length or width of the dosing end 14 and including a portion of the sides are also contemplated.

Body cover 20 and chamber cover 22 overly spacing layer 18 and define a slot 30 therebetween which provides a vent opening communicating with sample-receiving chamber 26 to allow air to escape sample-receiving chamber 26 as a sample fluid enters sample-receiving chamber 26 through opening 28. Slot 30 is located at a position relative to sample-receiving chamber 26 that is interior of the location of the electrode systems (described below) positioned in sample-receiving chamber 26. Sample fluid entering sample-receiving chamber 26 will progress as far as the vent opening, but no further. When viewed from the top, the slot provides a visual indication of a "fill-line" to confirm that the electrode systems in sample-receiving chamber 26 have been properly wetted or covered to function properly. Additionally or alternatively, dose sufficiency electrodes may also be positioned adjacent slot 30 to detect when the sample fluid has progressed to slot 30 to assure that wetting of the measuring electrodes has occurred. Other alternative configurations of test strip architectures are also anticipated that would include the required electrodes for two assays and the application of a sample with means for venting. The alternative architectures may include additional features such as means for detecting sample sufficiency or other electrodes for corrections or failsafes.

Other than the electrode systems and reagent materials, sample-receiving chamber 26 may be empty or may alternatively include a sorbent material. Suitable sorbent materials include polyester, nylon, cellulose, and cellulose derivatives such as nitrocellulose. When included, a sorbent material helps facilitate uptake of the sample fluid by assisting in wicking the fluid into sample-receiving chamber 26. The use of a sorbent material would also serve to further reduce the void volume of sample-receiving chamber 26 for reception of the sample fluid. In one form, the filling of sample-receiving chamber 26 occurs by capillary action. The filling of sample-receiving chamber 26 can also be augmented by other means, such as by applying a pressure on the sample fluid to push it into sample-receiving chamber 26, and/or creating a vacuum on sample-receiving chamber 26 to pull the sample fluid into sample-receiving chamber 26. In addition, one or more surfaces of sample-receiving chamber 26 can be formed from a hydrophilic material, provided with a coating of a hydrophilic material, or subjected to a hydrophilicity increasing treatment in order to facilitate filling of sample-receiving chamber 26 with the test sample.

Test element 10 is configured to detect the presence of, and/or measure the concentration of, first and second analytes by way of electrochemical oxidation and reduction reactions. These reactions are transduced to an electrical signal that can be correlated to an amount or concentration of the analyte. As shown in FIG. 2, where only some features of test element 10 are illustrated, substrate 16 carries a first electrode system 32 that includes a plurality of electrodes 34 and electrode traces 36 terminating in contact pads 38. Electrodes 34 are defined as those portions of electrode traces 36 that are positioned within sample-receiving chamber 26. Substrate 16 also carries a second electrode system 46 that includes a plurality of electrodes 48 and electrode traces 50 terminating in contact pads 52. Electrodes 48 are defined as those portions of electrode traces 50 that are positioned within sample-receiving chamber 26. It should be understood that the illustrated configurations of electrode systems 32, 46 are not limiting, and that alternative configurations are contemplated.

Test element 10 also includes a first reagent material 60 which overlies at least a portion of electrodes 34 of first electrode system 32 within sample-receiving chamber 26, and a second reagent material 62 which overlies at least a portion of electrodes 48 of second electrode system 46 within sample-receiving chamber 26. First and second reagent materials 60, 62 are suitable for producing electrochemical signals in the presence of respective first and second test analytes, and are disposed within sample-receiving chamber 26 in position to provide the electrochemical signal to electrodes 34, 48 in sample-receiving chamber 26. In the illustrated form, a space 64 extends between first and second reagent materials 60, 62, although forms in which space 64 is absent and first and second reagent materials form a continuous layer over electrodes 34, 48 are also contemplated. Further details regarding first and second reagent materials 60, 62 will be provided herein below.

Electrodes 34 of first electrode system 32 include a set of measuring electrodes in the form of working electrode 40 and counter electrode 42 which includes portions 44a and 44b spaced on opposite sides of working electrode 40. As used herein, a "working electrode" is an electrode at which an analyte is electrooxidized or electroreduced with or without the agency of a redox mediator, while the term "counter electrode" refers to an electrode that is paired with the working electrode and through which passes an electrochemical current equal in magnitude and opposite in sign to the current passed through the working electrode. The term "counter electrode" is meant to include counter electrodes which also function as reference electrodes (i.e., counter/reference electrodes). Electrodes 48 of second electrode system 46 include a set of measuring electrodes in the form of working electrode 54 and counter electrode 56 which includes portions 58a and 58b spaced on opposite sides of working electrode 54. In this arrangement, sample-receiving chamber 26 is configured such that sample fluid entering sample-receiving chamber 26 is placed in electrolytic contact with working electrodes 40 and 54 and counter electrodes 42 and 56. This arrangement also allows electrical current to flow between the measuring electrodes to affect the electrooxidation or electroreduction of the first and second analytes. It should be appreciated however that the foregoing is only one of a number of configurations for the measuring electrodes.

Figure 3:
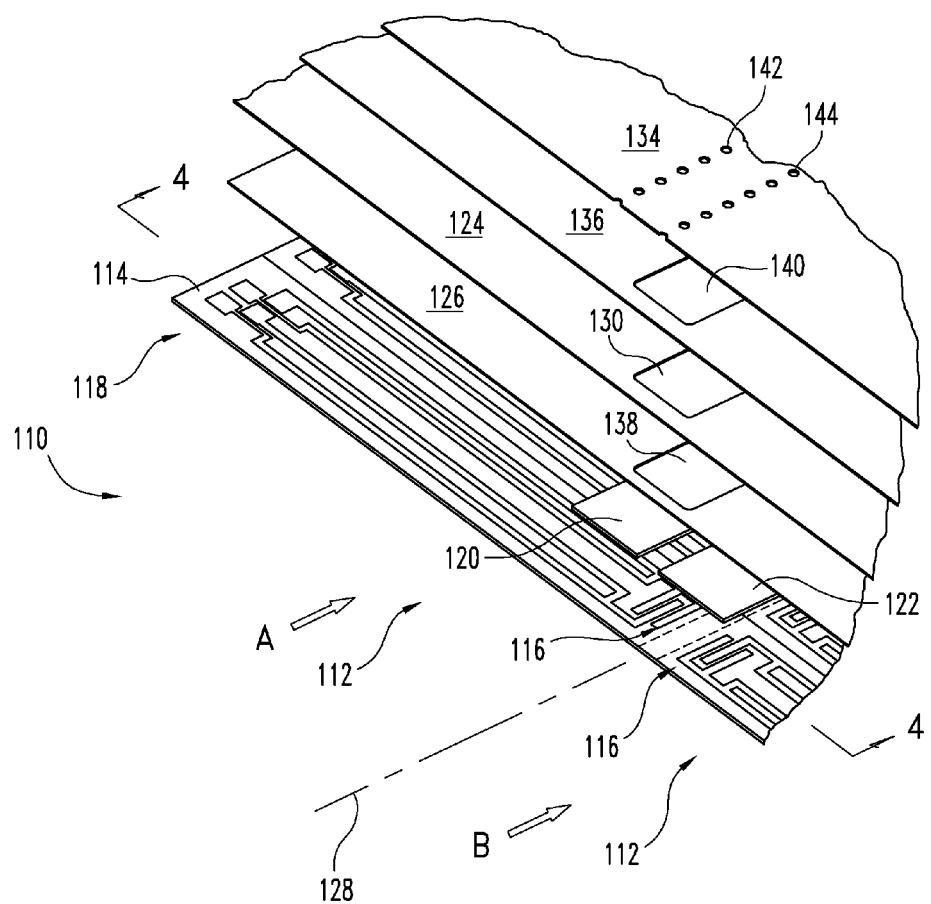
FIG. 3 is an exploded, perspective view of a second embodiment test element.
Figure 4:
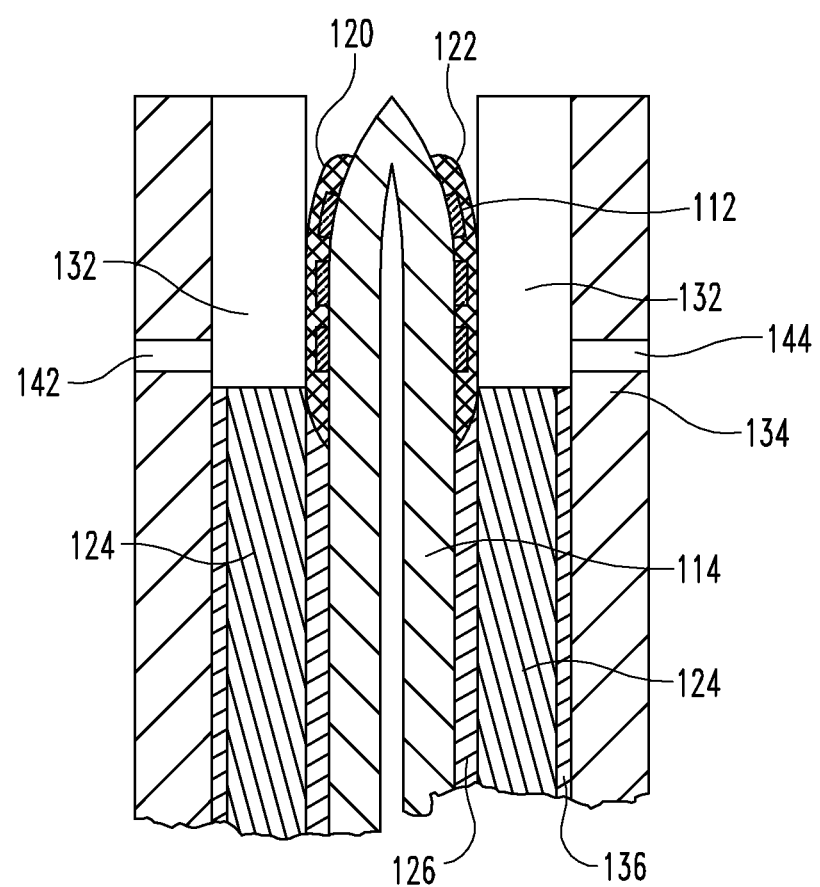
FIG. 4 is a fragmentary, sectional view of the test element of FIG. 3.

An alternative embodiment test element 110 for assessing first and second analytes in a sample is illustrated in FIGS. 3 and 4. Test element 110 is produced utilizing a head to head manufacturing technique. Further details of this technique, and of test element 110 generally, are found in International Patent Publication No. WO 2012/003306, the contents of which are incorporated herein by reference in their entirety. As illustrated in FIG. 3, electrode patterns 112 are arranged in two columns (one set of electrode patterns in column A and one set in column B) on an elongated layer (tape) of a substrate 114. Test element 110 also includes sample chamber electrode patterns 116 located near each other and near the center of substrate 114 and contact pads 118 spaced apart from one another and located near the opposite edges of substrate 114. In the illustrated form, the electrode patterns are all similar; however in alternative forms at least some of the electrode patterns may be different from other electrode patterns. A first reagent material 120 is applied over the sample chamber electrodes 116 in column A and a second reagent material 122 is applied over the sample chamber electrodes 116 in column B.

A spacer layer 124 is attached to the top of substrate 114 with an adhesive layer 126. In the illustrated form, one elongated strip or tape forms spacer layer 124 to cover the electrode patterns of both columns A and B, although forms in which two separate strips of spacer layer 124 are individually attached to substrate 114 in column A and column B and aligned along centerline 128 are also possible. Spacer layer 124 includes a plurality of cutout portions 130 arranged along centerline 128. When spacer layer 124 is assembled with substrate 114, cutout portions 130 will form the perimeters of sample chambers 132 (FIG. 4). A single, continuous upper substrate layer 134 is attached to the top of spacer layer 124 with an adhesive layer 136 and includes a plurality of vent openings 142, 144 to facilitate venting of sample chambers 132 as they are filled with a sample fluid. While not previously discussed, it should be appreciated that adhesive layers 126, 136 include a plurality of cutout portions 138, 140, respectively, arranged along centerline 128 and corresponding to cutout portions 130 of spacer layer 124. Alternatively, it is contemplated that adhesive layer 136 may be a solid layer without any openings or cutouts.

After substrate 114, reagent materials 120, 122, spacer layer 124 and upper substrate 134 are combined and laminated together, the sheet or roll is separated such that electrodes patterns 116 in columns A and B remain attached to one another while the test strips in adjacent rows (side-by-side oriented test strips) are separated. In other words, the test strips in column A are not fully separated from the test strips in column B, and test strip pairs are formed with each pair of test strips arranged in a head-to-head manner. Each test strip pair may be folded to place contact pads 118 of the test strip from column A adjacent contact pads 118 of the test strip from column B, and to place the sampling end of the test strip from column A adjacent to and facing the same direction as the sampling end of the test strip from column B. Using this type of head-to-head test strip pair, a dual-use biosensor is provided in which a user can apply a sample of bodily fluid to both test strips simultaneously in order to test for first and second different analytes using a single sample. In one embodiment, a blood filtering media may be provided within dual sample chambers 132 prior to folding the pair together in order to prevent blood and reagent mixing between chambers 132.

It should be appreciated that chambers 132 in each of the head-to-head oriented pair of test strips should be exposed when the pair of test strips are bent along centerline 128. Alternative manufacturing techniques can be used to ensure both sample chambers 132 are exposed. For example, in one embodiment, one of the substrate layers, e.g. top layer 134, is fully separated along centerline 128 during manufacture while the substrate 114 is either unmodified or modified to predictably bend about centerline 128. In an alternative embodiment, one of the substrate layers is modified, such as through perforations or partial cutting to be easily separated by the user along centerline 128 while the other substrate is modified, such as by scoring, denting or crimping, to predictably bend or separate about a straight line, for example, centerline 128. In still another embodiment, both top layer 134 and lower substrate 114 are modified to allow the head-to-head test strips to be folded in either direction, i.e., the user may choose to bend the head-to-head pair of test strips to have top layers 134 of the two test strips positioned adjacent one another or to have substrates 114 of the two test strips positioned adjacent one another.

Substrates 16, 114 may be formed of an insulating material on which electrode systems 32, 46 and electrode patterns 112, respectively, are positioned. Typically, plastics such as vinyl polymers, polyimides, polyesters, and styrenes provide the electrical and structural properties which are required. Further, because the test elements can be mass producible from rolls of material, it is desirable that the material properties be appropriate to have sufficient flexibility for roll processing, while also giving a useful stiffness to the finished element. The material for substrates 16, 114 can be selected as a flexible polymeric material such as polyester, including high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). One specific material possible for substrates 16, 114 is MELINEX® 329 available from duPont.

The working and counter electrodes, and the remaining portions of the electrode systems 32, 46 and electrode patterns 112, may be formed from a variety of materials. In one aspect, the electrodes should have a relatively low electrical resistance and should be electrochemically inert over the operating range of the test elements. Suitable conductors for the working electrode include gold, palladium, platinum, carbon, titanium, ruthenium dioxide, and indium tin oxide, and iridium, as well as others. The counter electrode may be made of the same or different materials, e.g., silver/silver chloride. In one specific embodiment, the working and counter electrodes are both gold electrodes.

Electrode systems 32, 46 and electrode patterns 112 may be applied to substrates 16, 114, respectively, in any fashion that yields electrodes of adequate conductivity and integrity. Exemplary processes include sputtering and printing, just to provide a few non-limiting possibilities. In one specific form, gold electrodes are provided by coating the materials of substrates 16, 114 and then removing selected portions of the coating to yield the electrode systems 32, 46 and electrode patterns 112. One particular method for removing portions of the coating include laser ablation, and more particularly broad field laser ablation, as disclosed in U.S. Pat. No. 7,073,246, the contents of which are incorporated herein by reference in their entirety.

Laser ablative techniques typically include ablating a single metallic layer or a multi-layer composition that includes an insulating material and a conductive material, e.g., a metallic-laminate of a metal layer coated on or laminated to an insulating material. The metallic layer may contain pure metals, alloys, or other materials, which are metallic conductors. Examples of metals or metallic-like conductors include: aluminum, carbon (such as graphite), cobalt, copper, gallium, gold, indium, nickel, palladium, platinum, silver, titanium, mixtures thereof, and alloys or solid solutions of these materials. In one aspect, the materials are selected to be essentially unreactive to biological systems, non-limiting examples of which include gold, platinum, palladium, carbon and iridium tin oxide. The metallic layer may be any desired thickness which, in one particular form, is about 500 nm.

It should be understood that the illustrated form of test elements 10, 110 is not-limiting, and that alternative configurations for the dual function test elements of the subject application, including those arranged for optical detection techniques, are also contemplated. In this regard, in one additional and non-limiting form a dual function test element may include a sandwich-type of configuration where a first substrate that carries a first electrode system is positioned over a second substrate that carries a second electrode system. The first and second substrates are spaced apart from one another by an intermediate layer that includes a capillary channel or a capillary channel is otherwise formed between the first and second substrates. In this configuration, sample fluid that enters into the capillary channel is directed toward the first and second electrode systems such that simultaneous or near simultaneous covering of the first and second electrode systems occurs. While not previously discussed, it should be further understood that the first substrate is provided with a first reagent material suited for determination of a first analyte and that the second substrate is provided with a second reagent material suited for determination of a second analyte. By way of non-limiting example, one technique for producing test elements having this configuration involves separately producing the first substrate carrying the first reagent material and the first electrode system and the second substrate carrying the second reagent material and the second electrode system and then assembling the first and second substrates together.

In another non-limiting form, a dual function test element may include a slightly different sandwich-type of configuration. In this configuration, a first substrate that carries a first electrode system is positioned over a second substrate that carries a second electrode system. However, the first and second substrates are joined by an adhesive layer and each includes a separate sample chamber positioned over its respective electrode system in lieu of a single capillary channel. In this form, the test element includes a configuration that facilitates simultaneous or near simultaneous filling of the individual sample chambers such that simultaneous or near simultaneous covering of the first and second electrode systems also occurs. While not previously discussed, it should be further understood that the first substrate is provided with a first reagent material suited for determination of a first analyte and that the second substrate is provided with a second reagent material suited for determination of a second analyte. This test element may also be produced utilizing the technique discussed above in connection with the other sandwich-type of configuration described herein. Further details of one non-limiting test element having this form are provided in International Patent Publication No. WO 2012/003306 (incorporated herein above).

Further examples of non-limiting arrangements that may be utilized for the test element of the subject application are disclosed in U.S. Pat. Nos. 6,984,307 and 4,397,956, the contents of which are incorporated herein by reference in their entirety.

It is contemplated that test elements 10, 110 may be useful for the determination of a wide variety of first and second analytes from a biological fluid. For example, test elements 10, 110 may be readily adapted for use with reagent materials 60, 62 and 120, 122 having any suitable chemistry that can be used to assess the presence and/or concentration of the first and second analytes. Reagent materials 60, 62 and 120, 122 are operable for reacting with the first and second analytes to produce the electrochemical signals that represent the presence and/or concentration of the first and second analytes in the sample fluid. As will be discussed in greater detail below, reagent materials 60, 62 and 120, 122 can include a variety of active components selected to determine the presence and/or concentration of various first and second analytes. The test chemistries of reagent materials 60, 62 and 120, 122 are therefore selected in respect to the first and second analytes to be assessed. Such analytes may include, for example, glucose, cholesterol, HDL cholesterol, triglycerides, glycerine, lactates, lactate dehydrogenase, malates, alcohol, uric acid, sorbitol, amino acids, 1,5-anhydroglucitol and analytes representative of ketone bodies, such as hydroxybutyrate. In one particular embodiment, test elements 10, 110 include reagent materials 60, 62 and 120, 122, respectively, which are selected to determine the presence and/or concentration of hydroxybutyrate and glucose in blood.

Non-limiting examples of biological fluids in which the first and second analytes can be assessed include any bodily fluid in which the analytes can be measured, such as interstitial fluid, tears, urine, and blood. The term "blood" in the context of this document includes whole blood and its cell-free components, namely plasma and serum. When the test elements are configured for the testing of hydroxybutyrate and glucose, the sample fluid may specifically include, for example, fresh capillary blood obtained from the finger tip or approved alternate sites (e.g., forearm, palm, ear lobe, upper arm, calf and thigh), fresh venous blood or urine. In addition, the test elements may also be useful in connection with control fluids that are used in conventional fashion to verify the integrity of the system for testing.

The bodily fluid containing the analyte to be assessed may be acquired and delivered to the test elements in any fashion. For example, a blood sample may be obtained in conventional fashion by incising the skin, such as with a lancet, and then contacting the test element with fluid that appears at the skin surface. In one aspect, the test elements are operable for assessing the targeted analyte while only using very small fluid samples. Similarly, in one aspect, only a slight skin incision is necessary to produce the volume of fluid required for the test, and the pain and other concerns with such method can be minimized or eliminated.

Reagent materials 60, 120 include a first coenzyme-dependent enzyme or a substrate for the first enzyme and a suitable coenzyme. These components are typically dissolved or suspended in a matrix. The liquid test sample hydrates or dissolves the matrix, and the first analyte diffuses through the matrix to react with one or more of the active components. Suitable enzymes that could be included in reagent materials 60, 120 are for example dehydrogenases selected from glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1, 1.6), alcohol dehydrogenase (E.C.1.1.1.1), hydroxybutyrate dehydrogenase (HBDH), such as 3-hydroxybutyrate dehydrogenase or beta-hydroxybutyrate dehydrogenase, alpha-hydroxybutyrate dehydrogenase and gamma-hydroxybutyrate dehydrogenase, sorbitol dehydrogenase, and amino acid dehydrogenase e.g. L-amino acid dehydrogenase (E.C.1.4.1.5). Further suitable enzymes are oxidases such as glucose oxidase (E.C.1.1.3.4) or cholesterol oxidase (E.C.1.1.3.6) or aminotransferases such as aspartate or alanine aminotransferase, 5'-nucleotidase or creatine kinase. Depending on the selected enzyme, potential coenzymes suitable for use in reagent materials 60, 120 include FAD, NAD, NADP, thio-NAD, thio-NADP, and a compound according to formula (I)

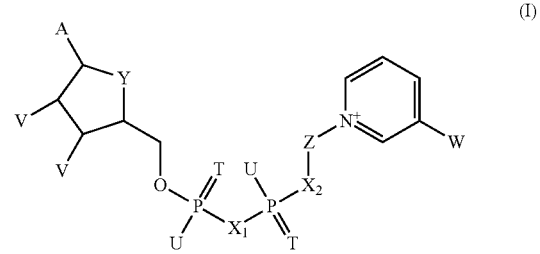

(I)

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group, W=COOR, CON(R)$_2$, COR, or CSN(R)$_2$ in which R in each case independently denotes H or C$_1$-C$_2$-alkyl, X$_1$, X$_2$=in each case independently denote O, CH$_2$, CHCH$_3$, C(CH$_3$)$_2$, NH, or NCH$_3$, Y=NH, S, O, or CH$_2$, Z=a residue comprising a cyclic group with 5 C atoms which optionally contains a heteroatom selected from O, S and N and optionally one or more substituents, and a residue CR4$_2$ wherein CR4$_2$ is bound to the cyclic group and to X$_2$, and where R4=in each case independently denotes H, F, Cl, or CH$_3$, provided that Z and the pyridine residue are not linked by a glycosidic bond, or a salt or optionally a reduced form thereof.

In one embodiment, W=CONH$_2$ or COCH$_3$.

Exemplary substituents on Z are selected from the group consisting of OH, F, Cl, and C$_1$-C$_2$ alkyl which are optionally fluorinated or chlorinated and/or OH-substituted, O—C$_1$-C$_2$-alkyl.

In another embodiment, a first residue V is OH and a second residue V is a phosphate group. Optionally, the one OH group and the one phosphate group can form a ring together with the carbon atoms to which they are bound.

Non-limiting examples of adenine analogues include C$_8$-substituted and N$_6$-substituted adenine, deaza variants such as 7-deaza aza variants such as 8-aza or combinations such as 7-deaza or 8-aza or carbocyclic analogues such as formycin where the 7-deaza variants can be substituted in the 7 position with halogen, C$_1$-C$_6$-alkinyl, C$_r$-C$_6$-alkenyl or C$_1$-C$_6$-alkyl. In a further embodiment the compounds contain adenosine analogues which contain for example 2-methoxydeoxyribose, 2'-fluorodeoxy-ribose, hexitol, altritol or polycyclic analogues such as bicyclic, LNA and tricyclic sugars instead of ribose. In one form, (di)phosphate oxygens can also be isoelectronically substituted such as for example O$^-$ by S$^-$ and/or by BH$_3^-$, O by NH, NCH$_3$ and/or by CH$_2$ and =O by =S. In one embodiment at least one residue U of a compound according to formula (I) is different from OH and in other embodiments at least one residue U=BH$_3^-$.

Another more particular but non-limiting compound according to formula (I) in which:

A=adenine,
T=in each case denotes O,
U=in each case denotes OH,
V=in each case denotes OH,
W=CON(R)$_2$ in which R denotes H,
X$_1$=O,
X$_2$=O,
Y=O, and
Z=a carbocyclic 5-membered ring of the general formula (II)

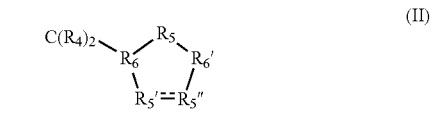

in which a single bond is present between R5' and R5", and in which
R4=H,
R5'=CHOH,
R5"=CHOH,
R5=CR4$_2$,
R6=CH, and
R6'=CH
is carba-NAD or cNAD.
carba-NAD has the following structure:

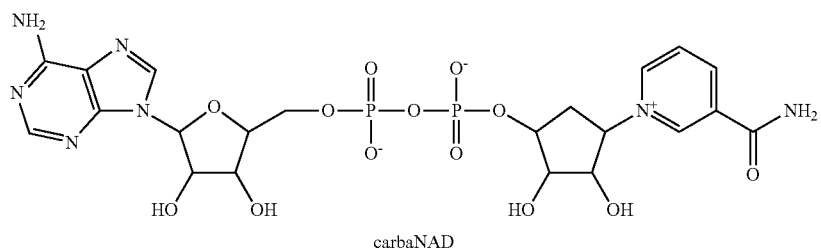 [SMILES: NC(=O)c1ccc[n+](C2CC(OP(=O)([O-])OP(=O)([O-])OCC3OC(n4cnc5c(N)ncnc54)C(O)C3O)C(O)C2O)c1]

carbaNAD

Yet another more particular but non-limiting compound according to formula (I) in which:

A=adenine,
T=in each case denotes O,
U=in each case denotes OH,
V=in a first case denotes OH and in a second case denotes a phosphate group,
W=CON(R)$_2$ in which R denotes H,
X$_1$=O,
X$_2$=O,
Y=O, and
Z=a carbocyclic 5-membered ring of the general formula (II)

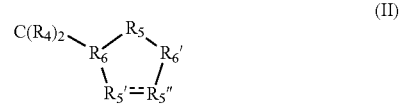

in which a single bond is present between R5' and R5", and in which
R4=H,
R5'=CHOH,
R5"=CHOH,
R5=CR4$_2$, R6=CH, and
R6'=CH
is carba-NADP or cNADP.
carba-NADP has the following structure:

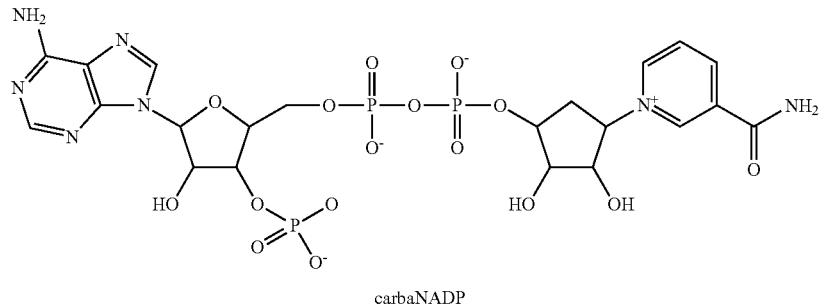 [SMILES: NC(=O)c1ccc[n+](C2CC(OP(=O)([O-])OP(=O)([O-])OCC3OC(n4cnc5c(N)ncnc54)C(O)C3OP(=O)([O-])O)C(O)C2O)c1]

carbaNADP

Other particular but non-limiting compounds according to formula (I) include borano carba-NAD, cyclopentyl NAD, and carba-NAD cyclophosphate. These compounds have the following structures:

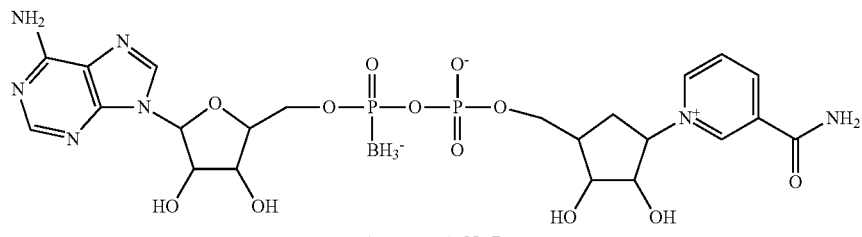

borano carbaNAD

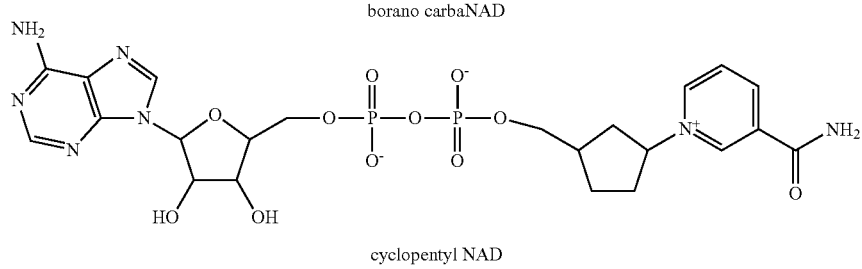

cyclopentyl NAD

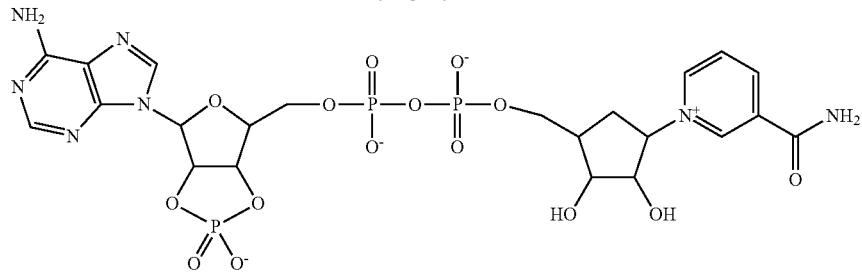

carbaNAD cyclophosphate

Further details regarding compounds according to formula (I) and synthesis of the same are provided in U.S. Patent Publication No. 2008/0231809, the contents of which are incorporated herein by reference in their entirety.

In one embodiment, reagent materials 60, 120 are operable to facilitate detection of the presence and/or concentration of hydroxybutyrate and include a hydroxybutyrate dehydrogenase. Non-limiting examples of hydroxybutyrate dehydrogenase include alpha-hydroxybutyrate dehydrogenase, beta or 3-hydroxybutyrate dehydrogenase, and gamma-hydroxybutyrate dehydrogenase. In one particular form, the hydroxybutyrate dehydrogenase is 3-hydroxybutyrate dehydrogenase. In this embodiment, reagent materials 60, 120 further include a coenzyme selected from thio-NAD, thio-NADP, and a compound according to formula (I) or a salt or optionally a reduced form thereof. In one particular form, reagent materials 60, 120 include 3-hydroxybutyrate dehydrogenase and one of carbaNAD and carbaNADP. In forms where the first reagent material includes a hydroxybutyrate dehydrogenase and a coenzyme selected from thio-NAD, thio-NADP, and a compound according to formula (I) or a salt or optionally a reduced form thereof, it has been surprisingly discovered that detection of the presence and/or concentration of hydroxybutyrate can be completed in or about five seconds after the test element has been contacted with the sample, which generally corresponds to state of the art glucose testing which takes about five seconds. Further details in this regard and in connection with preparation of related reagent materials are provided in a U.S. Patent Application filed on the same date herewith, entitled "Reagent Materials and Associated Test Elements" and having Ser. No. 13/667,057, the contents of which are incorporated herein by reference in their entirety. It should be understood that the use of reagent materials that require more than five seconds to complete detection of the presence and/or concentration of hydroxybutyrate are also suitable for use in test elements of the subject application.

In addition, while the use of a reagent material that includes a hydroxybutyrate dehydrogenase and a coenzyme selected from thio-NAD, thio-NADP, and a compound according to formula (I) or a salt or optionally a reduced form thereof has been described herein in connection with test elements having dual functionalities, it should be understood that the use of this reagent material in connection with test elements having single functionality is also possible. Non-limiting examples of additional forms of test elements for which use of this reagent material is contemplated are disclosed in U.S. Patent Application Publication No. 2005/0016844 and U.S. Pat. No. 7,008,799, the contents of which are hereby incorporated herein by reference in their entirety. It should also be appreciated that the reagent material does not require any additional enzymes, such as diaphorase, to be operable for the detection of presence and/or concentration of hydroxybutyrate in forms where it includes a hydroxybutyrate dehydrogenase and a coenzyme selected from thio-NAD, thio-NADP, and a compound according to formula (I) or a salt or optionally a reduced form thereof. However, inclusion of additional enzymes within the first reagent material is also contemplated.

The first reagent material may also include a mediator. The mediator can be selected as any chemical species (generally electroactive) which can participate in a reaction scheme involving the enzyme, the first analyte, and the coenzyme, and reaction products thereof, to produce a detectable electroactive reaction product. Typically, participation of the mediator in the reaction involves a change in its oxidation state (e.g., a reduction), upon interaction with any one of the first analyte, the enzyme, or the coenzyme, or a species that is a reaction product of one of these (e.g., a coenzyme reacted to a different oxidation state). A variety of mediators exhibit suitable electrochemical behavior. A mediator can preferably also be stable in its oxidized form, may optionally exhibit reversible redox electrochemistry, can preferably exhibit good solubility in aqueous solutions, and preferably reacts rapidly to produce an electroactive reaction product. Examples of mediators include benzoquinone, meldola blue, transition metal complexes such as potassium ferricyanide and osmium derivatives (see International Patent Publication No. WO 98/35225), a phenazine derivative, and hexaammineruthenium chloride or a combination thereof (see U.S. Pat. No. 8,008,037). The first reagent material may also include a nitrosoaniline-based compound that acts as a mediator precursor (see e.g. U.S. Pat. No. 5,286,362). In this regard, the nitrosoaniline-based mediator precursor breaks down into reversible mediator components when it contacts an analyte sample such as blood.

Additional examples of mediators and nitrosoaniline-based mediator precursors include N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3,4-tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, and N-(2-hydroxyethyl)-N-(2-(2-hydroxyethoxy)-ethyl)-4-nitrosoaniline.

Reagent materials 62, 122 include a second coenzyme-dependent enzyme or a substrate for the second enzyme and a suitable coenzyme. These components are typically dissolved or suspended in a matrix. The liquid test sample hydrates or dissolves the matrix, and the analyte diffuses through the matrix to react with one or more of the active components. Suitable enzymes that could be included in reagent materials 62, 122 are for example dehydrogenases selected from glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1, 1.6), alcohol dehydrogenase (E.C.1.1.1.1), hydroxybutyrate dehydrogenase (HBDH), such as 3-hydroxybutyrate dehydrogenase or beta-hydroxybutyrate dehydrogenase, alpha-hydroxybutyrate dehydrogenase and gamma-hydroxybutyrate dehydrogenase, sorbitol dehydrogenase, and amino acid dehydrogenase e.g. L-amino acid dehydrogenase (E.C.1.4.1.5). Further suitable enzymes are oxidases such as glucose oxidase (E.C.1.1.3.4) or cholesterol oxidase (E.C.1.1.3.6) or aminotransferases such as aspartate or alanine aminotransferase, 5'-nucleotidase or creatine kinase. Depending on the selected enzyme, potential coenzymes suitable for use in reagent materials 62, 122 include FAD, NAD, NADP, thio-NAD, thio-NADP, and a compound according to formula (I) or a salt or optionally a reduced form thereof.

In one embodiment where reagent materials 60, 120 are operable to facilitate detection of the presence and/or concentration of hydroxybutyrate, reagent materials 62, 122 are operable to facilitate detection of the presence and/or concentration of glucose and include an enzyme for glucose. In one particular form, the enzyme is a glucose dehydrogenase or a glucose oxidase. In this embodiment, reagent materials 62, 122 further include a coenzyme selected from FAD, NAD, NADP and the compound according to formula (I) or a salt or optionally a reduced form thereof. While not previously discussed, forms in which reagent materials 60 and 62 have a common coenzyme, e.g., a compound according to formula (I) or a salt or optionally a reduced form thereof, and are merged together to form a single reagent layer such that space 64 therebetween is eliminated are contemplated. It should also be understood that the reagent materials described herein for detecting the presence and/or concentration of glucose are not limiting, and that other forms for the same are known in the art. Additional non-limiting examples of reagent materials operable for detecting the presence and/or concentration of glucose are disclosed in U.S. Pat. No. 7,727,467 (incorporated herein above) and U.S. Pat. No. 8,008,037, the contents of which are incorporated herein by reference in their entirety. The second reagent material may also include a mediator. The mediator can be selected as any chemical species (generally electroactive) which can participate in a reaction scheme involving the second enzyme, the second analyte, and the coenzyme, and reaction products thereof, to produce a detectable electroactive reaction product. Typically, participation of the mediator in the reaction involves a change in its oxidation state (e.g., a reduction), upon interaction with any one of the second analyte, the second enzyme, or the coenzyme, or a species that is a reaction product of one of these (e.g., a coenzyme reacted to a different oxidation state). A variety of mediators exhibit suitable electrochemical behavior. A mediator can preferably also be stable in its oxidized form, may optionally exhibit reversible redox electrochemistry, can preferably exhibit good solubility in aqueous solutions, and preferably reacts rapidly to produce an electroactive reaction product. Examples of mediators include benzoquinone, meldola blue, transition metal complexes such as potassium ferricyanide and osmium derivatives (see International Patent Publication No. WO 98/35225), a phenazine derivative, and hexaammineruthenium chloride or a combination thereof (see U.S. Pat. No. 8,008,037). The second reagent material may also include a nitrosoaniline-based compound that acts as a mediator precursor (see e.g. U.S. Pat. No. 5,286,362). In this regard, the nitrosoaniline-based mediator precursor breaks down into reversible mediator components when it contacts an analyte sample such as blood.

Additional examples of mediators and nitrosoaniline-based mediator precursors include N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3,4-tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, and N-(2-hydroxyethyl)-N-(2-(2-hydroxyethoxy)-ethyl)-4-nitrosoaniline.

The reagent materials may also include a variety of adjuvants to enhance various properties or characteristics thereof. See e.g., U.S. Pat. No. 7,749,437 referred to hereinabove. For example, reagent materials 60, 62 and 120, 122 may include materials to facilitate their placement onto respective substrates 16, 114 and to improve their adherence thereto, or for increasing the rate of hydration of the reagent materials by the sample fluid. Additionally, the reagent materials can include components selected to enhance the physical properties of the resulting dried reagent layer, and the uptake of a liquid test sample for analysis. Examples of adjuvant materials to be used with the reagent materials include thickeners, viscosity modulators, film formers, stabilizers, buffers, detergents, gelling agents, fillers, film openers, coloring agents, and agents endowing thixotropy.

Non-limiting examples of thickeners that may be included in the reagent materials include (1) starches, gums (e.g., pectin, guar gum, locust bean (carob seed) gum, konjac gum, xanthan gum, alginates, and agar), casein, gelatin, and phycocolloids; (2) cellulose and semi-synthetic cellulose derivatives (carboxymethyl-cellulose, methyl cellulose, hydroxymethylcellulose, hydroxyethylcellulose, methylhydroxyethylcellulose); (3) polyvinyl alcohol and carboxyvinylates; and (4) bentonite, silicates, and colloidal silica. More specific forms of thickeners include a combination of a xanthan gum sold under the trade name Keltrol F by CP Kelco US, Inc., and carboxylmethyl cellulose sold under the trade name AQUALON® CMC 7F PH by Hercules Inc., Aqualon Division.

Film forming and thixotropic agents that can be included in the reagent materials include polymers and silica. One more specific thixotropic agent includes silica sold under the trade name Kieselsaure Sipemate FK 320 DS by Degussa AG, while a more specific film forming agent includes polyvinylpyrrolidone, sold under the trademark polyvinylpyrrolidone Kollidon 25, by BASF, and polyvinyl propionate dispersion.

Stabilizers for the enzymes in the reagent materials can be selected from sacchhrides and mono- or di-fatty acid salts. More specific stabilizers include trehalose sold under the trade name D-(+)-Trehalose dihydrate by Sigma Chemical Co. and sodium succinate.

Non-limiting examples of detergents that can be included in the reagent materials include water-soluble soaps, as well as water-soluble synthetic surface-active compounds such as alkali, earth alkali or optionally substituted ammonium salts of higher fatty acids, e.g., oleic or stearic acid, mixtures of natural fatty acids, for example, from coconut or tallow oil, fatty sulphates, esters of sulphonic acids, salts of alkyl sulphonic acids taurine salts of fatty acids, fatty acid amides, and ester amides. More specific forms of detergents include an ester amide, n-octanoyl-N-methylglucamide, sold under the trade name Mega-8 by Dojindo Molecular Technologies, Inc., and a fatty acid salt, N-methyl oleyl taurate sodium salt, sold under the trade name Geropon T77 by Rhodia HPCII (Home, Personal Care and Industrial Ingredients).

In one form, the reagent materials are formulated as a viscous solution that includes thickeners and thixotropic agents to enhance its physical properties. The thickeners are selected to provide a thick, liquid matrix having the remaining components homogeneously dispersed therein. The thickening and thixotropic agents also inhibit the liquid or semi-paste material from running or spreading over the surface of substrates 16, 114 after it has been deposited and before it dries. After the reagent materials are deposited, they quickly dry to a readily hydratable matrix.

As indicated above, it has been surprisingly discovered that detection of the presence and/or concentration of hydroxybutyrate can be completed in or about five seconds after the test element has been contacted with the sample in forms where the first reagent material includes a hydroxybutyrate dehydrogenase and a coenzyme selected from thio-NAD, thio-NADP, and a compound according to formula (I) or a salt or optionally a reduced form thereof. Current state of the art for glucose testing facilitates the detection of the presence and/or concentration of glucose to be completed in or about five seconds after the test element has been contacted with the sample. U.S. Pat. No. 8,008,037 describes one non-limiting form of glucose testing that facilitates detection of the presence and/or concentration of glucose within this timeframe. Additional, non-limiting forms of glucose testing that facilitates detection of the presence and/or concentration of glucose within this timeframe are described in U.S. Pat. Nos. 7,276,146 and 7,276,147, the contents of both being hereby incorporated herein by reference in their entirety. It should be understood however that other reagent materials which facilitate detection of the presence and/or concentration of glucose within this or other timeframes are known and could be used in the test elements disclosed herein.

In view of the foregoing, it should be appreciated that detection of the presence and/or concentration of hydroxybutyrate and glucose can be completed within five seconds after the test element has been contacted by the sample when the test element includes a first reagent material that has a hydroxybutyrate dehydrogenase and a coenzyme selected from thio-NAD, thio-NADP, and a compound according to formula (I) or a salt or optionally a reduced form thereof, and a second reagent material that is suitable for detection of glucose and appropriately formulated. However, it should also be understood that variations in the timing for completing the detection of hydroxybutyrate and glucose with these test elements is also possible and dependent on, for example, the specific formulation of the reagent materials, amongst other aspects. In one form for example, the detection of hydroxybutyrate and glucose is completed within 10 seconds after the test element has been contacted by the sample. In another form, the detection of hydroxybutyrate and glucose is completed within 7.5 seconds after the test element has been contacted by the sample. It should also be appreciated that the timing for completion of the hydroxybutyrate detection and the glucose detection may be different. For example, in one or more of the foregoing or other forms the hydroxybutyrate detection is completed within 4 seconds before or after completion of the glucose detection. In another variant, the hydroxybutyrate detection is completed within 2 seconds before or after completion of the glucose detection. In still another variant, the hydroxybutyrate detection is completed at or near the same time the glucose detection is completed. It should be understood however that other variations in the timeframe for completion of hydroxybutyrate and glucose detection are contemplated.

Figure 5:
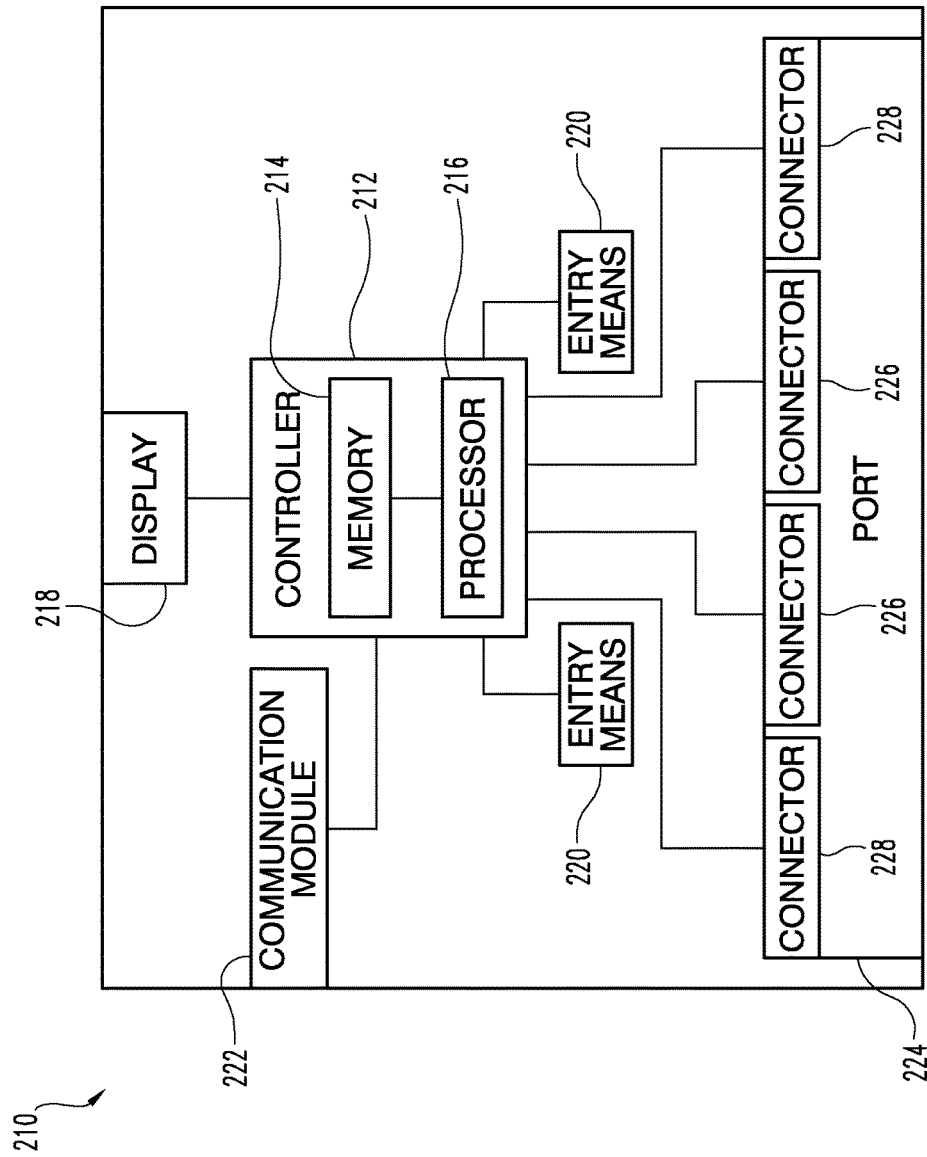
FIG. 5 is a schematic illustration of an analytical instrument structured for use with the test element of FIG. 1.

Turning now to FIG. 5, further details of one non-limiting analytical instrument in the form of a test meter 210 suitable for use with test element 10 will be provided. While test meter 210 is described for use with test element 10, it should be understood that it could be readily altered to accommodate use with test element 110 while retaining the general operating principles discussed below. Test meter 210 generally includes a controller 212, memory 214 associated with controller 212, and a programmable processor 216 associated with controller 212 and connected with memory 214. Test meter 210 also includes a display 218 connected with processor 216 with, for example, a display driver, and operable to provide a user readable display of output from processor 216. Processor 216 is connected with test element port 224 and operable to process and record data in memory 214 relating to the detection of the presence and/or concentration of the first and second analytes obtained through use of test element 10. Test element port 224 includes connectors 226 configured to engage with contact pads 38 of first electrode system 32 and connectors 228 configured to engage with contact pads 52 of second electrode system 46. Test meter 210 further includes user entry means 220 connected with processor 216 and accessible by a user to provide input to processor 216 and processor 216 is further programmable to receive input commands from user entry means 220 and provide an output that responds to the input commands.

Processor 216 is also connected with a communication module or link 222 to facilitate wireless transmissions with test meter 210. In one form, communication link 222 may be used to exchange messages, warnings, or other information between test meter 210 and another device or party, such as a caseworker, caregiver, parent, guardian or healthcare provider, including nurses, pharmacists, primary or secondary care physicians and emergency medical professionals, just to provide a few possibilities. Communication link 222 can also be utilized for downloading programming updates for test meter 210. By way of non-limiting example, communication link 222 may be configured for sending and receiving information through mobile phone standard technology, including third-generation (3G) and fourth-generation (4G) technologies, or through Bluetooth, Zigbee, Wibree, ultra-wide band (UWB), wireless local area network (WLAN), General Packet Radio Service (GARS), Worldwide Interoperability for Microwave Access (WiMAX or WiMAN), Wireless Medical Telemetry (WMTS), Wireless Universal Serial Bus (WUSB), Global System for Mobile communications (GSM), Short Message Service (SMS) or WLAN 802.11x standards.

Controller 212 may be comprised of one or more components configured as a single unit or of multi-component form. Controller 212 may be programmable, a state logic machine or other type of dedicated hardware, or a hybrid combination of programmable and dedicated hardware. One or more components of controller 212 may be of the electronic variety defining digital circuitry, analog circuitry, or both. As an addition or alternative to electronic circuitry, controller 212 may include one or more mechanical or optical control elements.

In one embodiment including electronic circuitry, controller 212 includes an integrated processor 216 operatively coupled to one or more solid-state memory devices defining, at least in part, memory 214. For this embodiment, memory 214 contains operating logic to be executed by processor 216 that is a microprocessor and is arranged for reading and writing of data in memory 214 in accordance with one or more routines of a program executed by microprocessor 216.

Memory 214 may include one or more types of solid-state electronic memory and additionally or alternatively may include the magnetic or optical variety. For example, memory 214 may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), or Electrically Erasable Programmable Read Only Memory (EEPROM); or a combination of any of these types. Also, memory 214 may be volatile, nonvolatile or a hybrid combination of volatile and nonvolatile varieties. Some or all of memory 214 can be of a portable type, such as a disk, tape, memory stick, cartridge, code chip or the like. Memory 214 can be at least partially integrated with processor 216 and/or may be in the form of one or more components or units.

In other embodiments, it is contemplated that test meter 210 may utilize a removable memory key that is pluggable into a socket or other receiving means (not shown), and which communicates with the memory or controller of the meter 210 to provide information relating to calibration codes, measurement methods, measurement techniques, and information management. Examples of such removable memory keys are disclosed in U.S. Pat. Nos. 5,366,609 and 5,053,199, the disclosures of which are incorporated herein by reference in their entireties.

Controller 212 may also include signal conditioners, filters, limiters, Analog-to-Digital (A/D) converters, Digital-to-Analog (D/A) converters, communication ports, or other types of operators as would occur to those skilled in the art. Entry means 220 may be defined by a plurality of push-button input devices, although entry means 220 may include one or more other types of input devices like a keyboard, mouse or other pointing device, touch screen, touch pad, roller ball, or a voice recognition input subsystem. Display 218 may include one or more output means like an operator display that can be of a Cathode Ray Tube (CRT) type, Liquid Crystal Display (LCD) type, plasma type, Organic Light Emitting Diode (OLED) type, a printer, or the like. Other input and display means can be included such as loudspeakers, voice generators, voice and speech recognition systems, haptic displays, electronic wired or wireless communication subsystems, and the like.

As indicated above, test element port 224 includes connectors 226 configured to engage with contact pads 38 of first electrode system 32 and connectors 228 configured to engage with contact pads 52 of second electrode system 46. The connection between test meter 210 and test element 10 is utilized to apply a potential or a series of potentials across the electrodes of first and second electrode systems 32, 46, and to subsequently receive electrochemical signals that are produced by first and second reagent materials 60, 62 in the presence of the first and second analytes and can be correlated to the concentration of the first and second analytes. Processor 216 is configured to evaluate the electrochemical signals in order to assess the presence and/or concentration of the first and second analytes, and the results of the same may be stored in memory 214.

While not previously discussed, it should be understood that forms in which a first processor is used to evaluate the electrochemical signals associated with the first analyte and a second processor is used to evaluate the electrochemical signals associated with the second analyte are contemplated. In addition, when test element 10 is configured for facilitating electrochemical determination of sample presence and/or that the amount of the sample fluid is sufficient for testing, processor 216 may also be configured to assess electrochemical signals associated therewith to determine that the sample fluid has been received by the test element, and/or that the amount of sample fluid is sufficient for testing.

In one form, processor 216 is generally configured to automatically or seamlessly produce a signal for providing an indication from meter 210 related to the presence and/or concentration of the first and second analytes after the relevant electrochemical signals have been evaluated. In certain forms where the first and second analytes are hydroxybutyrate and glucose and the reagent materials are appropriately formulated, processor 216 may be configured such that test meter 210 is capable of providing the indication related to hydroxybutyrate and glucose analysis at the same time and with no or only minimal delay after the completion of either test. The indication provided by test meter 210 may be in the form of one or more tactile, aural and/or visual alarms, warnings, messages or other representations, just to provide a few possibilities. For example, in one particular but non-limiting form, processor 216 provides a signal to which display 218 is responsive to produce an indication related to the presence and/or concentration of the first and second analytes after the relevant electrochemical signals have been evaluated.

The indication produced by display 218 may include, for example, one or more of a quantitative indication or representation of the concentration of one or both of the first and second analytes, a qualitative indication or representation that one or both of the first and second analyte concentrations is acceptable, and a warning indication or representation that one or both of the first and second analyte concentrations is not acceptable. In this respect, processor 216 is configured to compare the measured values for the concentrations of the first and second analytes with a predetermined value or range of values for the first and second analytes stored in memory 214 for example, and determine if the concentrations of the first and second analytes are acceptable. For example, processor 216 might determine that the measured concentration of one or both of the first and second analytes is acceptable if it independently falls below a respective predetermined value or within a respective range of predetermined values, or that the concentration of one or both of the first and second analytes is unacceptable if it falls above the respective predetermined value or outside of the respective range of predetermined values. It should be understood that a single quantitative, qualitative or warning indication could be provided that covers the relevant analysis of the first and second analytes or that separate quantitative, qualitative or warning indications could be provided that independently cover the relevant analysis of the first and second analytes.

The qualitative indication may be in the form of an icon indicative of approval, such as a check mark, relevant text, relevant emoticon (e.g., smiley face), or thumbs up, or in the form of an icon indicative of disapproval or unacceptability, such as an "X"-mark, relevant text, relevant emoticon (e.g., frown face), or thumbs down, just to provide a few non-limiting possibilities. Additionally or alternatively, the qualitative indication may involve the use of a first color, shading or design of display 218 when the concentration of the first and second analytes is acceptable and a second color, shading or design of display 218 when the concentration of one or both of the first and second analytes is unacceptable. For example, the background of display 218 may be green when the concentration of the first and second analytes is acceptable and then change to red if and when the concentration of one or both of the first and second analytes is not acceptable. As another example, the background of display 218 may include a non-patterned configuration when the concentration of the first and second analytes is acceptable and a patterned configuration when the concentration of one or both of the first and second analytes is not acceptable. In still another example, display 218 may include a first section associated with analysis of the first analyte and a second section associated with analysis of the second analyte. In this arrangement, a color or pattern change of the background of display 218 may be associated with a single one of the first and second sections in the event only one of the first and second analyte concentrations is not acceptable. However, a color or pattern change of the background of display 218 will be associated with both of the first and second sections if the concentration of both of the first and second analytes is not acceptable. The first and second sections may utilize a common color or pattern change, or the color or pattern change associated with the first and second sections could be independent.

The warning indication may be accompanied by a tactile or aural alarm and/or a notice instructing the user of test meter 210 to seek immediate medical attention and/or to take one or more actions to address the unacceptable concentration of the first and/or second analytes. In one form, the warning indication includes an information icon and in response to its selection by a user of test meter 210, additional information such as an explanation of the reason for the warning, contact information for one or more healthcare providers or medical professionals, and/or a list of actions that need to be taken due to the unacceptable concentration of one or both of the first and second analytes may be provided on display 218. In certain forms, the information icon is not provided and this additional information may be automatically provided without any specific action required of the user of test meter 210.

In addition to or in lieu of display 218 or another component of meter 210 producing an indication related to the presence and/or concentration of the first and second analytes in response to a signal produced by processor 216, test meter 210 may be configured to provide the indication related to the presence and/or concentration of the first and second analytes to another device or party via communication link 222. In one exemplary form, processor 216 provides a signal to which communication link 222 is responsive to transmit a message including information related to the presence and/or concentration of the first and second analytes. This message may be sent to one or more other devices of the user of test meter 210 and/or to one or more devices of one or more third parties, such as a healthcare provider, caregiver, parent or guardian, just to provide a few non-limiting possibilities. Non-limiting examples of devices to which this message may be sent include PDA's, tablets, computers, pagers, and cellular and landline phones. In one form, the message may be sent directly to the one or more other devices of the user of test meter 210 and/or to the one or more devices of the one or more third parties, although forms in which the user of test meter 210 is first prompted to transmit the message are also envisioned. In another form, the message may additionally or alternatively be sent to a central computer or data processing unit which may store the message and/or transmit it on to one or more of the various devices identified above belonging to the user of test meter 210 or one or more other parties.

The information included in the message transmitted by communication link 222 may generally correspond to the indication that is described above and produced by display 218, and likewise may include one or more of the quantitative, qualitative and warning indications related to the presence and/or concentration of one or both of the first and second analytes. The devices to which the message is sent by communication link 222 may be configured to display this information in a manner corresponding to that described above in connection with display 218, although forms in which this information is alternatively displayed and/or reproduced are possible. It should be understood however that the message transmitted by communication link 222 may include information in addition to or in lieu of these indications. For example, in one form where the message is transmitted to a device of a third party, it may include a notice that the user of test meter 210 is in need of emergency medical assistance. In one particular aspect of this form, the message may also include information regarding the location and/or contact information of the user of test meter 210. Similarly, the third party to which the message is sent may directly or indirectly contact or locate the user of test meter 210 to provide assistance as necessary. Communication link 222 may also be configured to receive input from one or more of the devices of the one or more third parties.

Similarly, in response to receiving a message including information related to the concentration of one or both of the first analytes, such as one or both of these concentrations not being acceptable, one or more of the third parties may send a message to test meter 210 which is received by communication link 222 and in turn displayed on display 218. This message may include, for example, directions for the user of test meter 210 to contact a third party, such as an emergency medical professional, and/or to take certain actions to correct or otherwise address the unacceptable concentration of one or both of the first analytes. In certain forms, processor 216 is configured to provide signals or instructions for execution of different actions or functions by test meter 210 depending on, for example, the concentration determined for the first and second analytes. For example, in one form where the first and second analytes are hydroxybutyrate and glucose, processor 216 is configured to automatically or seamlessly provide a signal after the relevant electrochemical signals have been evaluated to which display 218 is responsive to produce a quantitative representation of the glucose concentration but not of the hydroxybutyrate or representative ketone concentration. Display 218 could also be responsive to this signal to further provide a qualitative or warning indication related to the glucose concentration. Additionally or alternatively, one or more other components of test meter 210, such as communication link 222, audio speakers or other output means, may be responsive to this signal to provide a quantitative or qualitative output representative of the glucose concentration.

In one aspect of these forms, processor 216 is further configured to provide a signal for test meter 210 to provide quantitative, qualitative or warning information related to the measured hydroxybutyrate concentration. For example, one or more components of test meter 210, such as communication link 220, display 218, audio speakers or other output means, may be responsive to this signal to provide quantitative, qualitative or warning information related to the measured hydroxybutyrate concentration. In one non-limiting form, display 218 is responsive to the signal to produce a qualitative or warning indication related to the measured hydroxybutyrate concentration. As illustrated in FIG. 6A for example, display 218 produces a qualitative indication that includes a first background color of display 218, such as green, and relevant text 230 specifying "Ketone OK" when the measured hydroxybutyrate concentration is acceptable; e.g., it is below a predetermined value or falls within a range of predetermined values. When the measured hydroxybutyrate concentration is not acceptable, e.g., it is above the predetermined value or falls outside the range of predetermined values, display 218 produces a warning indication that involves a change in background color of display 218 from the first color to a second color such as red, and in relevant text 230 to specify "Warning High Ketone (Take Action)". Display 218 could also provide a quantitative representation of hydroxybutyrate concentration with the warning indication.

Another variation in displaying the qualitative and warning indications related to the measured hydroxybutyrate concentration is shown in FIGS. 7A and 7B. As illustrated, display 218 includes a first section 232a associated with the quantitative representation of the glucose concentration, and a second section 232b associated with the qualitative and warning indications related to the measured hydroxybutyrate concentration. In this configuration, second section 232b of display 218 produces a qualitative indication that includes a first background color of display 218 at second section 232b, such as green, and a relevant emoticon 234a in the form of a smiley face indicating an acceptable hydroxybutyrate concentration when the hydroxybutyrate concentration is acceptable. When the measured hydroxybutyrate concentration is not acceptable, second section 232b of display 218 produces a warning indication that involves a change in background color of display 218 at second section 232b from the first color to a second color such as red, and from emoticon 234a to an emoticon 234b indicative of disapproval, such as a frown face. Display 218 could also provide a quantitative representation of hydroxybutyrate concentration with the warning indication in this configuration.

Still, it should be appreciated that other variations in displaying the qualitative and warning indications related to the measured hydroxybutyrate concentration are possible. In addition, it is also contemplated that the qualitative and warning indications related to the measured hydroxybutyrate concentration could include an information icon that is selectable by a user of test meter 210. In response to selecting this icon, test meter 210 provides additional information related to the unacceptable hydroxybutyrate concentration, such as the contact information for one or more healthcare providers or medical professionals who should be contacted in light of the unacceptable hydroxybutyrate concentration, and/or a list of actions that need to be taken or activities to avoid in order to correct or otherwise address the unacceptable hydroxybutyrate concentration. While not previously discussed, it should also be appreciated that processor 216 may be configured to provide a signal to which communication link 222 is responsive to transmit a message, as described above, related to the qualitative and warning indications associated with the measured hydroxybutyrate concentration.

In another aspect of forms where, after the relevant electrochemical signals have been evaluated, processor 216 is configured to automatically or seamlessly provide a signal to which one or more components of test meter 210, such as communications link 222, display 218, audio speakers or other output means, is responsive to provide a quantitative output representative of the glucose concentration, processor 216 is further configured to produce a signal to which one or more components of test meter 210 is responsive to provide an output related to the hydroxybutyrate concentration if and only if it is not acceptable; e.g., it is above a predetermined value or falls outside a range of predetermined values. In this configuration, the concentration of hydroxybutyrate is determined for each test performed by test meter 210, but the user of test meter 210 is only bothered or burdened by indications or information related to the hydroxybutyrate concentration if there is a health concern. In one form however, even in this configuration the system may record into memory or otherwise store both the glucose and hydroxybutyrate concentrations with appropriate context such as date, time, and marked notes from the user.

In certain embodiments, it is contemplated that access to stored data would enable meter functionality that would allow the user to graphically or in a tabulated format see the results of one or both analytes over a period of time such as hours, days, weeks, or months. In certain aspects of these forms, meter 210 or another device may also be configured to monitor for trends in the measured analyte concentrations through review of historical data. Such monitoring may look for a variety of different trends, including for example, trends suggestive of the onset or likely onset of DKA and more subtle trends such as higher glucose and/or hydroxybutyrate levels on the weekends and better control during the week. In the latter instance, this may be a lifestyle driven result and indicate that the patient does not watch or maintain his or her diabetes well during the relevant timeframe, and providing notice of the same may help a diabetic user modify their behavior during these times. This advanced functionality that searches or monitors for various trends could be a feature of a meter that runs automatically, by request of the patient or user, or a feature that is managed by a health care professional through data that is downloaded to an EMR. Such retrospective data analysis could also be run on a secondary device such as a smart phone application that receives the data from the analytical device.

Turning to FIG. 8 for example, test meter 210 is configured such that display 218 includes a first section 236 where a quantitative representation of the glucose concentration is produced in response to the signal automatically provided by processor 216. First section 236 could also be responsive to this signal to further provide a qualitative or warning indication related to the glucose concentration. Display 218 also includes a second section 238 which is only provided or activated if and when the hydroxybutyrate concentration is not acceptable. In the illustrated form, the second section 238 provides a warning indication that includes relevant text specifying "Ketone High Alert (Take Action)". The warning indication of second section 238 also includes a different background color relative to that of first section 236. In a non-illustrated from, second section 238 may provide a quantitative representation of hydroxybutyrate concentration in addition to or in lieu of the warning indication if and when the hydroxybutyrate concentration is not acceptable. Still, it should be appreciated that other variations in first and second sections 236, 238 of display 218 are possible.

Figure 9:
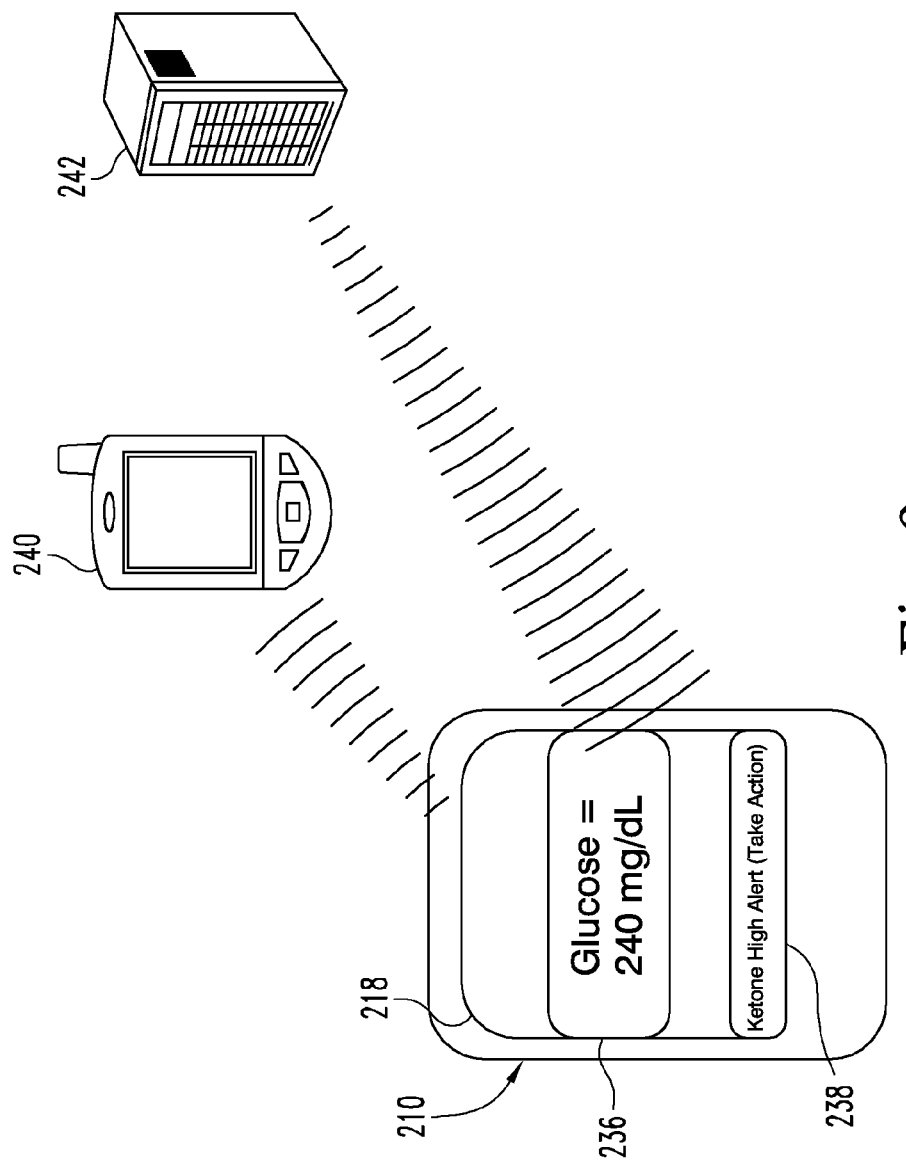
FIG. 9 is a schematic illustration of the analytical instrument communicating with other devices.

In addition, it is also contemplated that second section 238 could include an information icon that is selectable by a user of test meter 210. In response to selecting this icon, test meter 210 provides additional information related to the unacceptable hydroxybutyrate concentration, such as the contact information for one or more healthcare providers or medical professionals who should be contacted in light of the unacceptable hydroxybutyrate concentration, and/or a list of actions that need to be taken to correct or otherwise address the unacceptable hydroxybutyrate concentration. While not previously discussed, it should also be appreciated that processor 216 may be configured to provide a signal to which communication link 222 is responsive to transmit a message, as described above, related to the measured hydroxybutyrate concentration when it is not acceptable. For example, in the form shown in FIG. 9, communication link 222 transmits a message related to the measured hydroxybutyrate concentration to a separate device 240 in the form of a cellular phone which may belong to the user of test meter 210 or a third party. Device 240 could also be of a form other than a cellular phone, including those listed above, or the message could be transmitted to a plurality of devices having a variety of forms and belonging to a variety of different parties. Communication link 222 also transmits the message to a central computer or data processing unit 242 that may store the message and/or transmit it on to one or more of the other various devices. It should be appreciated that forms in which communication link 222 transmits the message to a single one of device 240 and data processing unit 242 are possible. In addition, while the illustrated form shows the message being transmitted in conjunction with the warning indication of second section 238 of display 218, forms in which the message is transmitted without production of the warning indication of second section 238 are possible. The information included in the message transmitted by communication link 222 may generally correspond to the information displayed by display 218. It should be understood however that the message transmitted by communication link 222 may include information in addition to or in lieu of that displayed by display 218. For example, in one form where the message is transmitted to a device of a third party, it may include a notice that the user of test meter 210 is in need of emergency medical assistance due to the unacceptable hydroxybutyrate concentration and the possible onset of an episode of DKA. In one particular aspect of this form, the message may also include information regarding the location (such as by providing GPS coordinates) and/or contact information of the user of test meter 210. Similarly, the third party to which the message is sent may directly or indirectly contact or locate the user of test meter 210 to provide assistance as necessary. Communication link 222 may also be configured to receive input or instructions from one or more of the devices of the one or more third parties as discussed above.

In some embodiments, if the hydroxybutyrate level is only slightly elevated or if the glucose level exceeds a predetermined value, such as ~240 mg/dL, meter 210 may be configured to go into a "ketone watch" mode of recommending and/or prompting a user to test hydroxybutyrate every 4-6 hours. In one non-limiting form, upon initiation of and during the ketone watch, meter 210 may automatically display measured glucose and hydroxybutyrate levels regardless of their relationship with any pre-specified values. In one embodiment, meter 210 also begins to monitor for further increases or other notable trends in hydroxybutyrate levels before providing further notice. In such embodiments, the alarm/warning/message notice will only be activated if a sufficient amount of increase from the initial level is measured at subsequent measurements. Testing every 4-6 hours is a recommendation from ADA guidelines (http://www.diabetes.org/living-with-diabetes/complications/ketoacidosis-dka.html) if glucose levels exceed ~240 mg/dL or if a patient is ill (e.g. with a cold or the flu).

In further embodiments, meter 210 may be configured to monitor for specific criteria to activate a "ketone watch dog" mode in order to remind the user to perform tests at some frequency and/or at certain times to decrease the likelihood of or avoid an onset of DKA and/or to detect for the same. Noting trends in this direction could enable a patient to avoid full onset of DKA. A dual assay hydroxybutyrate/glucose test strip enables such a system to be practical and to not burden the diabetic user unless necessary. In yet further embodiments, display 218 includes at least one segment in which a visual indication is provided to a user to indicate that meter 210 is in the ketone watch mode or otherwise operating as a "ketone watch dog."

Figure 10A:
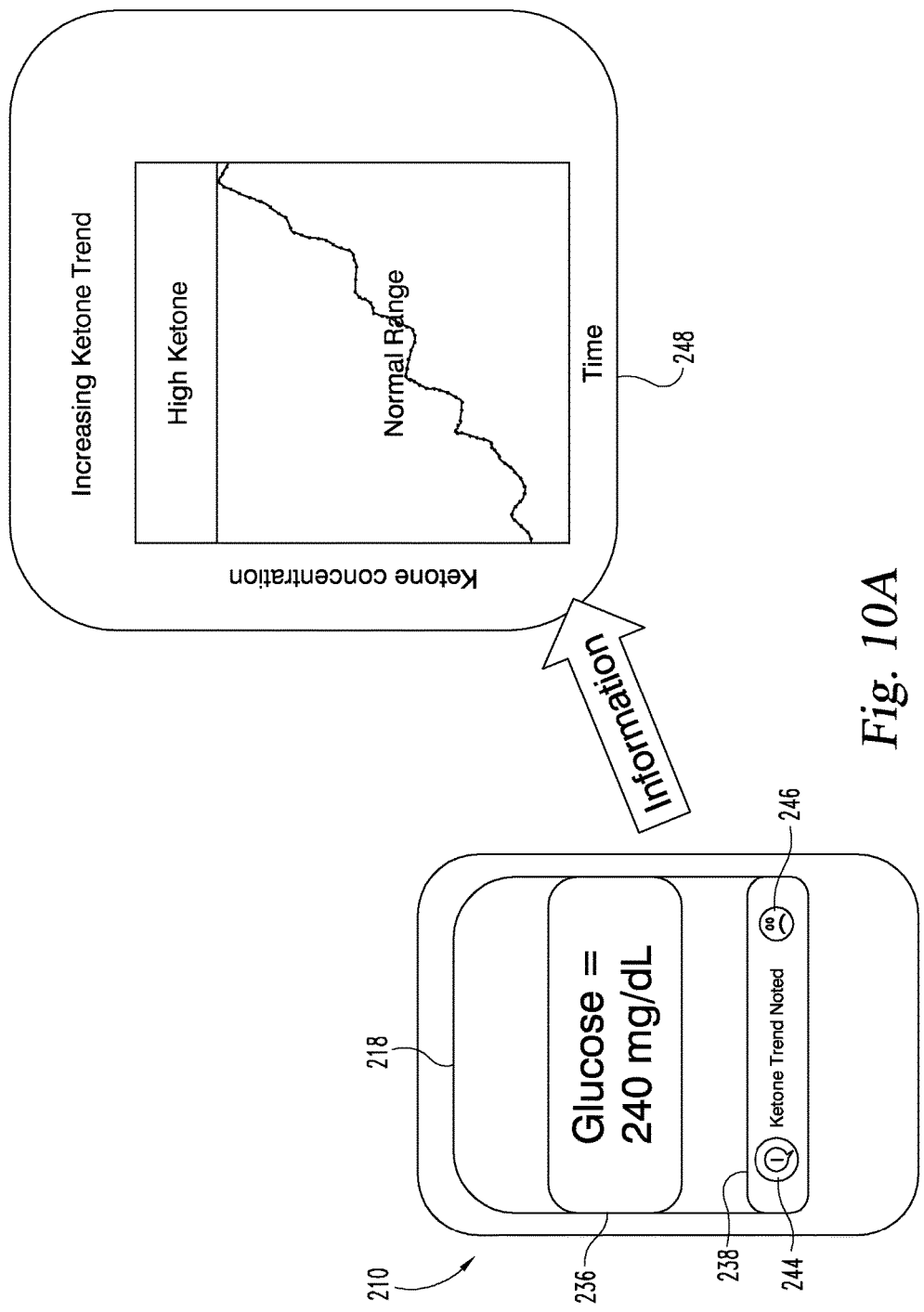
FIGS. 10A-E are schematic illustrations of another display configuration for the analytical instrument.

In addition to or in lieu of the foregoing, and as suggested above, meter 210 may also be further configured to analyze measured glucose or hydroxybutyrate concentrations to monitor for the existence of any trends. Such trends may include, without limitation, one or more of a trend moving toward a predetermined value or upwardly increasing over time toward an unacceptable level, trends between common time periods such as specific time of day, weekend trends, or after specific events like meals, exercise or illness, and any interesting rate-of-change trends suggesting concerning changes in glucose or hydroxybutyrate levels regardless of whether any such levels are measured to be above a predetermined value. For example, in one non-limiting form test meter 210 may be configured to store the results of each hydroxybutyrate concentration test in memory 214. Processor 216 is structured to analyze these results by, for example, producing a graphical representation of the measured hydroxybutyrate concentrations over time and monitoring for, amongst others, a trend in the graphical representation toward an unacceptable, predetermined value for the hydroxybutyrate concentration. Upon observing a trend of this nature (e.g. an upward rate of change of hydroxybutyrate), processor 216 is structured to provide a signal to which one or more components of test meter 210, such as communications link 222, display 218, audio speakers or other output means, is responsive to provide an output related to the upward trend in the hydroxybutyrate concentration. With reference to FIG. 10A for example, first section 236 of display 218 includes a quantitative representation of the measured glucose concentration and second section 238 of display 218 has been provided due to the observation of the upward trend in the hydroxybutyrate concentrations. Second section 238 includes relevant text specifying "Ketone Trend Noted". It also includes an information icon 244 and an emoticon 246 in the form of a frown face indicative of the undesired trend in hydroxybutyrate concentration. Forms in which second section 238 of display 218 only includes one or two of the relevant text, information icon 244 and emoticon 246 are also possible.

When information icon 244 is present as illustrated in FIG. 10A, it may be selected by a user of test meter 210 to provide additional information. For example, in the illustrated form, selection of information icon 244 results in the production of a graphical display 248 which shows increasing ketone or hydroxybutyrate levels over time. Graphical display 248 may also be automatically provided in addition to or in lieu of the information of second section 238. Graphical display 248 includes ranges representative of normal and high ketone levels, although it should be appreciated that other forms for graphical display 248 are possible. Test meter 210 may also provide information in addition to or in lieu of graphical display 248, including that described above in connection with the selection of an information icon. It should also be understood that second section 238 of display 218 can include a warning indication as described above if and when any test yields an unacceptable hydroxybutyrate concentration.

Figure 10B:
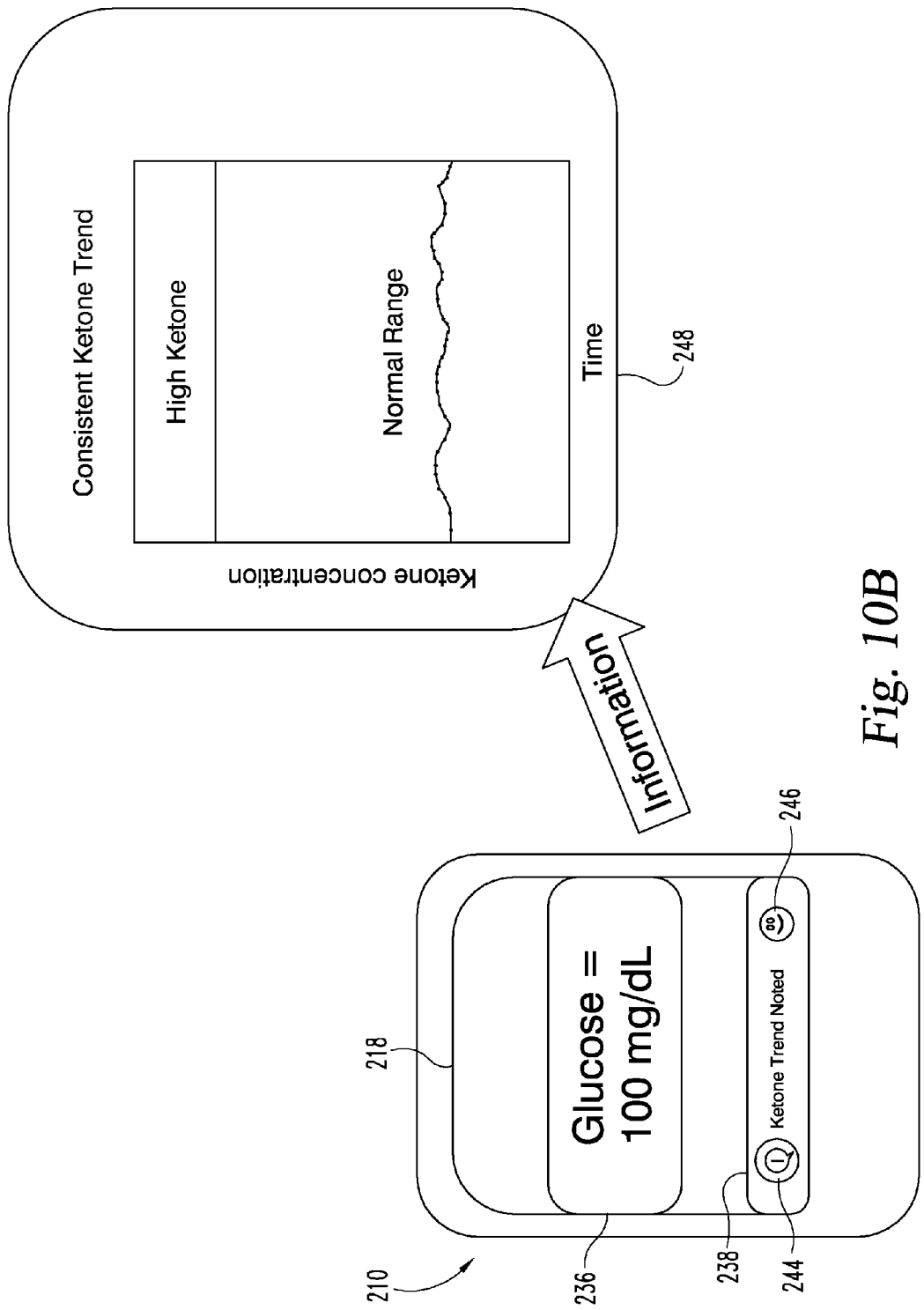
Figure 10C:
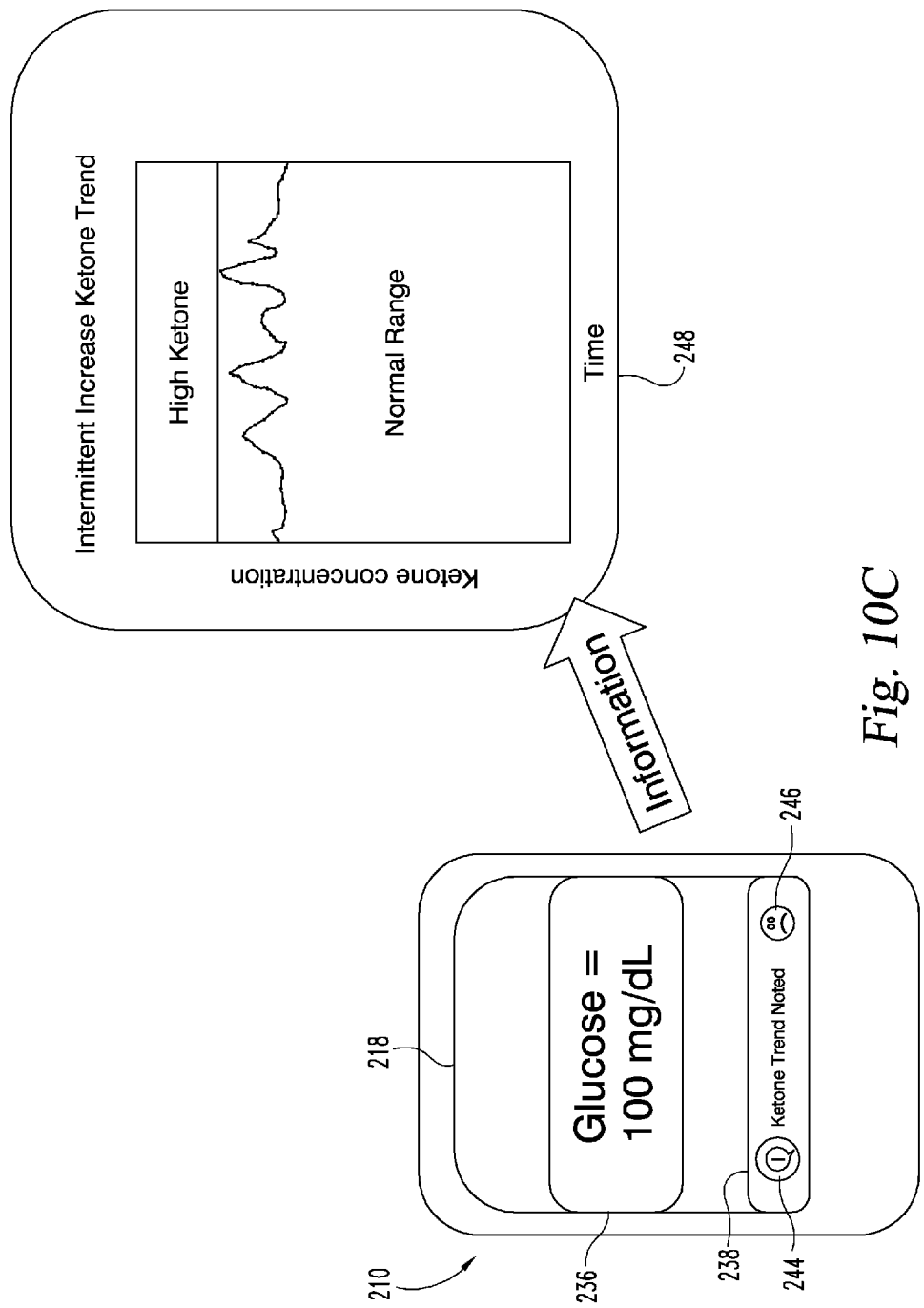
Figure 10D:
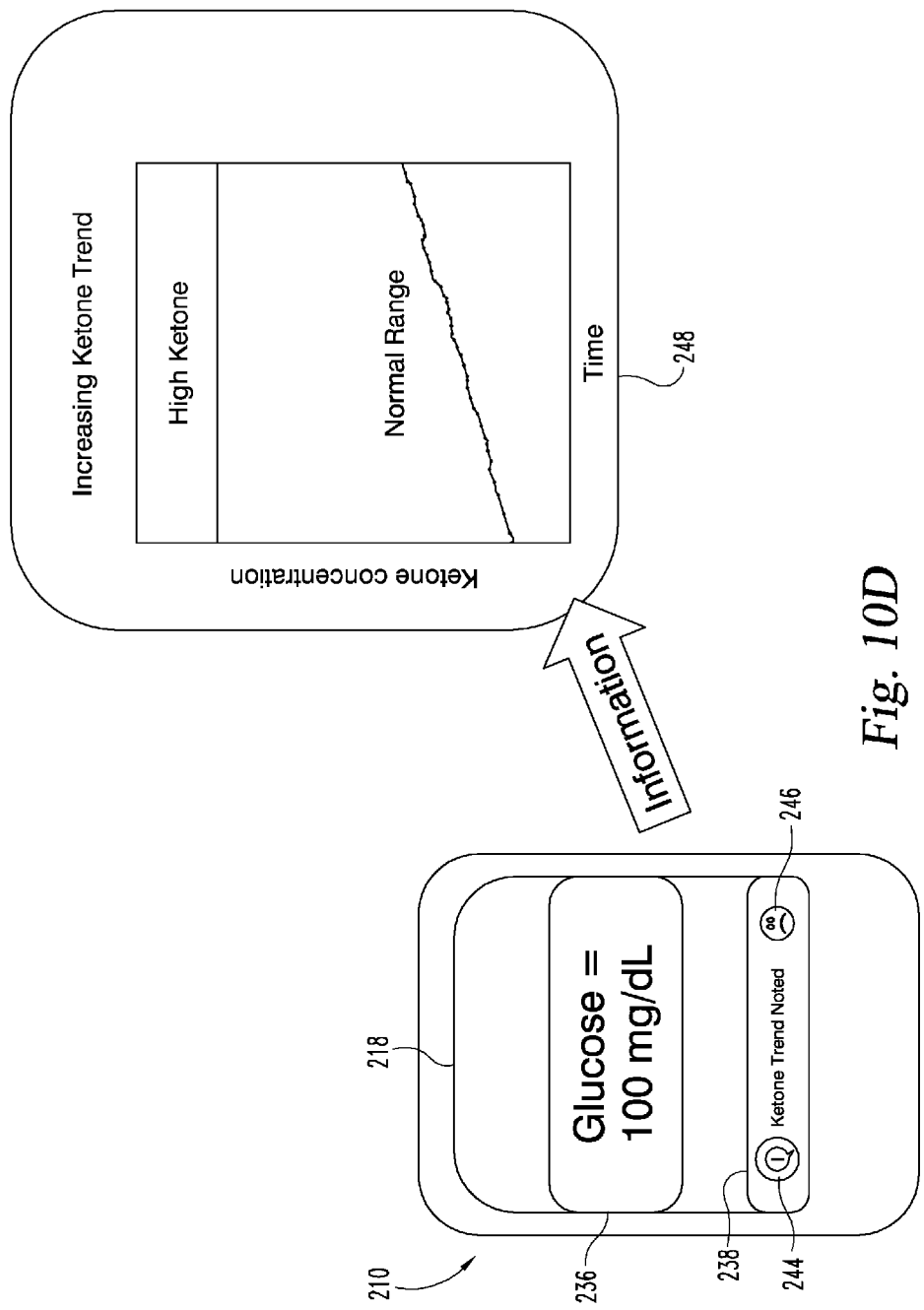
Figure 10E:
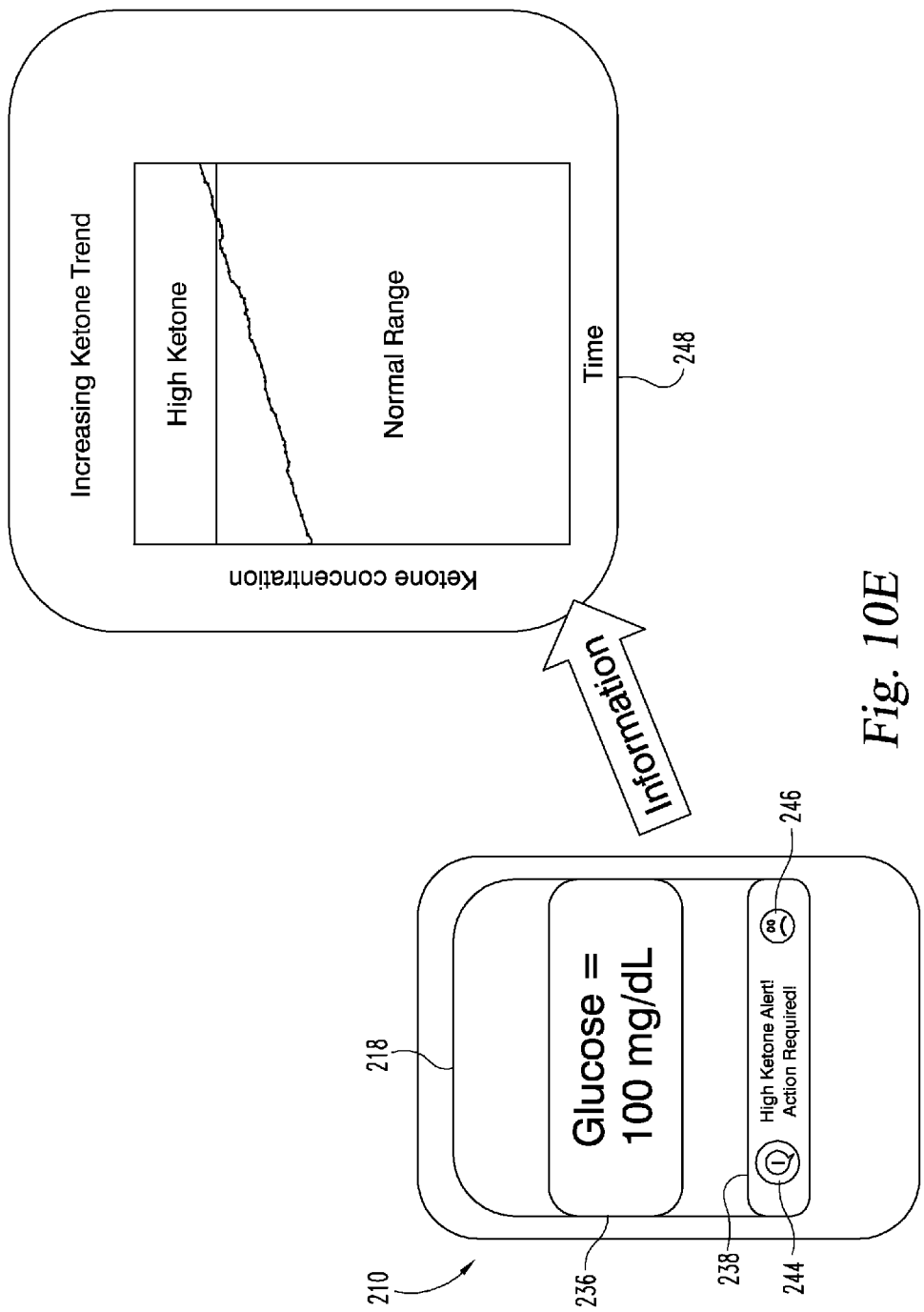

Moreover, while the provision of an output related to the observation of an upward trend in hydroxybutyrate concentration has been described in connection with forms of test meter 210 where output related to the hydroxybutyrate concentration is only provided when the hydroxybutyrate concentration is not acceptable, it should be appreciated that this type of output could also be provided in forms where test meter 210 is additionally or alternatively configured to provide indications related to the hydroxybutyrate concentration even when the same is deemed acceptable. For example, in FIG. 10B graphical display 248 is illustrative of an observed trend where measured hydroxybutyrate concentrations are relatively consistent over time. In FIG. 10C, graphical display 248 is illustrative of an observed trend where a number of spikes or increases in hydroxybutyrate concentration occur over time, while graphical display 248 in FIG. 10D is illustrative of an observed trend where measured hydroxybutyrate concentrations are moving toward an unacceptable value over time. In the case of FIG. 10B, graphical display 248 may provide positive reinforcement to a user of test meter 210 that their diabetes management is on an acceptable track. In the case of FIG. 10C for example, the observed increases or spikes in measured hydroxybutyrate concentrations shown in graphical display 248 may correspond to a certain event (such as a meal or exercise) or timeframe (such as the weekend) and provide notice to a user of meter 210 that a different management approach may be necessary at these times to avoid the intermittent increases. In FIG. 10D, the consistent increase shown by graphical display 248 provides notice to a user of meter 210 that continuing along the current trajectory will result in the onset of DKA and that remedial actions must be taken to avoid the same. In FIG. 10E, graphical display 248 shows that the upward trajectory has reached above the recommended high level at which DKA is likely imminent, and display 218 provides a clear alert warning that immediate action is required.

Despite being described in connection with hydroxybutyrate concentrations, it should be appreciated that the meter functionality discussed in connection with FIGS. 10A-D and elsewhere is also applicable to measured glucose concentrations. In addition, information related to any observed trend(s) of the hydroxybutyrate or glucose concentrations could also be transmitted by communication link 222 to one or more devices belonging to the user of test meter 210 or other third parties so that appropriate actions can be taken by necessary parties to address the observed trend(s).

In view of the foregoing, processor 216 may be structured in various forms to provide signals or instructions for the execution of certain actions based on the measured hydroxybutyrate concentration. For example, and without limitation, processor 216 may be structured such that a) the output provided by test meter 210 changes from a qualitative indication of acceptability of the measured hydroxybutyrate concentration to a warning indication of unacceptability of the measured hydroxybutyrate concentration when the hydroxybutyrate concentration exceeds a predetermined value or falls outside of a predetermined range of values; b) test meter 210 only provides an output related to the measured hydroxybutyrate concentration if and only if it is above a predetermined value or falls outside a range of predetermined values and is therefore not acceptable; and/or c) test meter 210 provides an output related to the observation of an upward trend of hydroxybutyrate concentrations toward an unacceptable, predetermined value for the hydroxybutyrate concentration. In one aspect, the predetermined value for triggering processor 216 to provide signals or instructions for the execution of certain actions based on the measured hydroxybutyrate concentration is in the range of 0.6 mM 3.0 mM. In another aspect, the predetermined value is 0.6 mM. For example, processor 216 may be structured such that a) the output provided by test meter 210 changes from a qualitative indication of acceptability to a warning indication of unacceptability of the measured hydroxybutyrate concentration when the hydroxybutyrate concentration exceeds 0.6 mM; b) test meter 210 only provides an output related to the measured hydroxybutyrate concentration if and only if it is above 0.6 mM; and/or c) test meter 210 provides an output related to the observation of an upward trend of hydroxybutyrate concentrations toward 0.6 mM.

In another aspect, processor 216 may be structured to provide signals or instructions for the execution of different actions or functions based on different hydroxybutyrate concentrations. In one non-limiting form for example, processor 216 may be configured to provide instructions for prompting execution of certain actions once the hydroxybutyrate concentration is at or exceeds 0.6 mM and other actions as the hydroxybutyrate concentration continues to rise above 0.6 mM. For example, when the hydroxybutyrate concentration is at or exceeds 0.6 mM but below 1.5 mM, processor 216 may be configured to provide instructions for activating, amongst other things, warning indications representative of an unacceptable ketone or hydroxybutyrate concentration. If the hydroxybutyrate concentration increases to a level between 1.5 mM and 3 mM, the actions executed in response to the instructions generated by processor 216 may also further include the transmittal of a message by communication link 222 to a caregiver, parent, guardian and/or non-emergency medical professional indicating, for example, that a risk is present for developing DKA. Once the hydroxybutyrate concentration reaches 3 mM, the actions executed in response to the instructions generated by processor 216 may also further include the transmittal of a message to an emergency medical professional that the user of test meter 210 requires immediate medical treatment. At this stage, the actions executed in response to the instructions generated by processor 216 may also further include transmittal of a message to a caregiver, parent, guardian and/or non-emergency medical professional indicating that the user of test meter 210 requires immediate medical attention. It should also be understood that the values provided above for having processor 216 generate instructions for the execution of the various different actions are exemplary only, and that one or more of the above-described actions may be executed in response to different hydroxybutyrate concentrations.

As an illustrative example, for hydroxybutyrate levels less than 0.6 mM, processor 216 in one embodiment is configured to cause conveyance of a message on display 218 indicating a "low" ketone level and that no action is required. In other embodiments, at such levels processor 216 causes the display to further convey the recommendation to monitor ketone change if the user is ill, and/or to perform both glucose and ketone tests every 4 hours. In another illustrative example, for hydroxybutyrate levels between 0.6 mM and 1.5 mM, processor 216 in one embodiment is configured to cause conveyance of a message on display 218 indicating a "medium" ketone level, and that a problem may be developing. In other embodiments, at such levels processor 216 causes display 218 to further convey the recommendation to consider instructions from the user's healthcare provider to notify him/her when such levels are detected. In yet another illustrative example, for hydroxybutyrate levels between 1.5 mM and 3.0 mM, processor 216 in one embodiment is configured to determine whether high glucose levels are also present and to cause conveyance of a message on display 218 recommending the user to contact the healthcare provider immediately. In yet another illustrative example, for hydroxybutyrate levels above 3.0 mM, processor 216 is configured to cause conveyance of a message on display 218 instructing the user to contact the healthcare provider immediately and/or to proceed to the emergency department of a clinic or hospital.

Additional recommended hydroxybutyrate level guidelines are also available in the available literature in this regard which can be used to configure appropriate rules employed by processor 216 for the display and messaging of a system in accordance with the various embodiments of the present invention. For example, according to one literature source, it is opined that under normal circumstances, hydroxybutyrate concentrations do not exceed 1 mM for Type I diabetic patients. In patients exhibiting DKA, the mean hydroxybutyrate concentration is about 7 mM but can range between 3 mM and 12 mM. Furthermore, when appropriate action is taken in response to high hydroxybutyrate concentrations, those concentrations should be expected to fall by 1 mM per hour, otherwise the treatment is likely inadequate and insulin and fluid infusion rates should be reviewed by the healthcare provider.

In addition to the foregoing, forms are also possible in which processor 216 is additionally or alternatively configured to provide instructions for executing one or more of the actions discussed above in response to determining that the hydroxybutyrate concentration is below a predetermined value.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method, comprising:
    performing a plurality of tests to determine concentrations of first and second analytes in a sample via a test meter configured to interact with test elements, wherein each of the tests includes applying the sample to a test element configured for electrochemically analyzing the first and second analytes in the sample, and wherein the first analyte is a ketone and the second analyte is glucose;
    storing, in a memory of the test meter, the first analyte concentration and the second analyte concentration determined from each test performed;
    automatically providing the second analyte concentration on at least a first portion of a display of the test meter from each test performed;
    analyzing the stored concentrations of the first analyte to monitor for an existence of an upwardly increasing trend in the stored concentrations toward a predetermined value of about 0.6 mM regardless of the second analyte concentration; and
    providing a first indication in response to detecting the existence of the trend on at least a second portion of the display screen of the test meter regardless of the second analyte concentration.

2. The method of claim 1, which further includes providing a second indication in response to determining the first analyte concentration is above the predetermined value in any one or more of the plurality of tests.

3. The method of claim 1, wherein the ketone is hydroxybutyrate.

4. The method of claim 1, wherein the first indication includes one of a graphical illustration of the trend and an information icon.

5. The method of claim 1, wherein providing the first indication includes displaying an information icon on a meter display.

6. The method of claim 5, which further includes providing a graphical illustration of the trend in response to a selection of the information icon.

7. The method of claim 1, further comprising automatically providing the concentration of the second analyte on at least a portion of the display screen of the test meter.

\* \* \* \* \*